US008962876B2

(12) United States Patent
Winter et al.

(10) Patent No.: US 8,962,876 B2
(45) Date of Patent: Feb. 24, 2015

(54) THERMALLY STABLE VOLATILE FILM PRECURSORS (75) Inventors: Charles H. Winter, Bloomfield Hills, MI (US); Thomas Joseph Knisley, Monroe, MI (US); Panditha Koralalage Don Mahesh Chinthaka Karunarathne, Panadura (SL)

(73) Assignee: Wayne State University, Detroit, MI (US)

( * ) Notice: Subject to any disclaimer, the term of this patent is extended or adjusted under 35 U.S.C. 154(b) by 385 days.

(21) Appl. No.: 13/319,793

(22) PCT Filed: May 17, 2010

(86) PCT No.: PCT/US2010/035080
§ 371 (c)(1),
(2), (4) Date: Nov. 10, 2011

(87) PCT Pub. No.: WO2010/132871
PCT Pub. Date: Nov. 18, 2010

(65) Prior Publication Data
US 2012/0058270 A1 Mar. 8, 2012

Related U.S. Application Data (60) Provisional application No. 61/178,734, filed on May 15, 2009.

(51) Int. Cl.
C07F 15/00 (2006.01)
C07F 13/00 (2006.01)
C07F 11/00 (2006.01)
C23C 16/18 (2006.01)
C07C 233/05 (2006.01)
C07F 15/02 (2006.01)
C07F 15/04 (2006.01)
C07F 15/06 (2006.01)
C07C 243/28 (2006.01)

(52) U.S. Cl.
CPC .............. C07C 233/05 (2013.01); C23C 16/18 (2013.01); C07F 11/005 (2013.01); C07F 13/005 (2013.01); C07F 15/025 (2013.01); C07F 15/045 (2013.01); C07F 15/065 (2013.01); C07C 243/28 (2013.01)
USPC ................. 556/146; 556/35; 556/45; 556/56; 556/57; 556/117; 427/255.26

(58) Field of Classification Search
CPC ...... C23C 16/18; C07F 11/005; C07F 13/005; C07F 15/025; C07F 15/045; C07F 15/065
USPC .......................... 556/35, 56, 57, 117, 45, 146; 427/255.26
See application file for complete search history.

(56) References Cited

U.S. PATENT DOCUMENTS

| 3,562,308 A | 2/1971 | Costa et al. |
| 5,721,014 A | 2/1998 | Fakler et al. |
| 6,020,511 A | 2/2000 | Vaartstra et al. |
| 6,786,936 B2 | 9/2004 | Vaartstra |
| 7,632,351 B2 | 12/2009 | Thompson |
| 2001/0009695 A1 | 7/2001 | Saanila et al. |
| 2002/0013487 A1 | 1/2002 | Norman et al. |
| 2002/0098346 A1 | 7/2002 | Yitzchaik |
| 2005/0097991 A1 | 5/2005 | Sanjurjo et al. |
| 2005/0186342 A1 | 8/2005 | Sager et al. |
| 2006/0134331 A1 | 6/2006 | Thompson |
| 2006/0157863 A1 | 7/2006 | Marsh |
| 2009/0114874 A1 | 5/2009 | Norman et al. |
| 2010/0104755 A1 | 4/2010 | Dussarrat et al. |
| 2010/0181566 A1 | 7/2010 | Lee |
| 2012/0231579 A1 | 9/2012 | Quick et al. |
| 2013/0115768 A1 | 5/2013 | Pore et al. |
| 2013/0251903 A1 | 9/2013 | Han |

FOREIGN PATENT DOCUMENTS

WO 2012027357 A2 3/2012

OTHER PUBLICATIONS

Thompson, Robert Kenneth. Amidate Complexes of the Group 4 Metals Synthesis, Reactivity, and Hydroaminiation Catalysis. Thesis. The Univerisy of British Columbia. http://hdl.handle.net/2429/1344. Available online Nov. 8, 2008. pp. 1-94 supplied.*
Hassaan, "Mixed ligand complexes of bis(s-methyl-n-arylidene hydrazine carbodithioate) nickel (ii) chelates with some amino acids and nitrogenous heterocycles," Journal of Islamic Academy [online] retrieved from http://www.medicaljournal-las.org/3_4/Hassaan.pdf on Jul. 1, 2010, pp. 269-272.
Pangani et al., "Coordination compounds of lanthanides with acetylhydrazine," Inorganica Chimca Acta, v. 94, issues 1-3, Feb. 1984, Abstract, p. 79.
Bart, S.C. et al., "Low-Valent α-Diimine Iron Complexes for Catalytic Olefin Hydrogenation," Organometallics 2005, v. 24, pp. 5518-5527.
d'Alnoncourt, R.N. et al., "The preparation of Cu/Al2O3 catalysts via CVD in a fluidized-bed reactor," Surface and Coatings Technology 201, pp. 9035-9904, 2007.
Dieck, H.T. et al., "Reaktionen von Bis(dizadien)eisen(O)," Komplexen. Chem. Ber., 120, pp. 1943-1950, Oct. 2002 (English Abstract).
Gardiner, M.G. et al., "Paramagnetic Bis(1,4-di-tert-butyl-1,4-diazabutadiene) Adducts of Lithium, Magnesium, and Zinc," Inorg. Chem. 1994, 33, pp. 2456-2461.
Ghosh, M. et al., "(α-Diimine)chromium Complexes: Molecular and Electronic Structures; a Combined Experimental and Density Functional Theoretical Study," Inorganic Chem., v. 47, No. 13, (2008), pp. 5963-5970.
Ghosh, M. et al., "A structural, spectroscopic and computational study of the molecular and electronic structure of a [bis(α-diiminato)manganese(II)] Π radical complex," Dalton Trans., 2008, pp. 5149-5151.

(Continued)

Primary Examiner — Porfirio Nazario Gonzalez
(74) Attorney, Agent, or Firm — Brooks Kushman P.C.

(57) ABSTRACT

A precursor for the deposition of a thin film by atomic layer deposition is provided. The compound has the formula MxLy where M is a metal and L is an amidrazone-derived ligand or an amidate-derived ligand. A process of forming a thin film using the precursors is also provided.

12 Claims, 3 Drawing Sheets

(56) References Cited

OTHER PUBLICATIONS

Gong, Y. et al., "The intra-annular acylamide chelate-coordinated compound: The keto-tautomer of metal (II)-milrinone complex," J. of Molecular Structure 875 (2008), pp. 113-120.

Hassaan, "Mixed ligand complexes of bis(s-methyl-n-arylidene hydrazine carbodithioate) nickel (ii) chelates with some amino acids and nitrogenous heterocycles," J. of Islamic Academy [online] retrieved from http://www.medicaljournal-las.org/3_4Hassaan.pdf on Jul. 1, 2010, pp. 269-272.

International Search Report dated Jul. 1, 2010 from corresponding PCT/US2010/035080 filed May 17, 2010, 2 pgs.

International Search Report for PCT/US2011/048792, Completed by the Korean Patent Office on Feb. 23, 2012, 3 pp.

International Search Report dated Aug. 17, 2012 from corresponding PCT/US12/040892 filed Jun. 5, 2012, pgs.

Kaltsoyannis, N., "Covalency in metal complexes of 1,4-diazabutadiene (dab). A density functional investigation of the electronic structures of [M(dab)2] (M=Li, Ga or Co) and [Th(NH3)NH2)3(dab)]," J. Chem. Soc., Dalton Trans., 1996, pp. 1583-1589.

Kalutarage, L.C. et al., "Low-Temperature Atomic Layer Deposition of Copper Films Using Borane Dimethylamine as the Reducing Co-reagent," Chem. Mater. 2014, 26, pp. 3731-3738.

Kalutarage, L.C. et al., "Synthesis, Structure, and Solution Reduction Reactions of Volatile and Thermally Stable Mid to Late First Row Transition Metal Complexes Containing Hydrazonate Ligands," Inorg. Chem. 2013, v. 52, pp. 5385-5394.

Kalutarage, L.C. et al., "Volatile and Thermally Stable Mid to Late Transition Metal Complexes Containing α-Imino Alkoxide Ligands, a New Strongly Reducing Coreagent, and Thermal Atomic Layer Deposition of Ni, Co, Fe, and Cr Metal Films," J. Am. Chem. Soc. 2013, 135, pp. 12588-12591.

Karunarathne, M.C. et al., "Exceptional thermal stability and high volatility in mid to late first row transition metal complexes containing carboyhydrazide ligands," Polyhedron 52 (2013), pp. 820-080.

Khusniyarov, M. M. et al., "Reversible Electron Transfer Coupled to Spin Crossover in an Iron Coordination Salt in the Solid State," Angew. Chem. Int. Ed. 2008, 47, pp. 1228-1231.

Khusniyarov, M.M. et al., "Molecular and Electronic Structures of Homoleptic Nickel and Cobalt Complexes with Non-Innocent Bulky Diimine Ligands Derived from Fluorinated 1,4-Diaza-1,3-butadiene (DAD) and Bis(arylimino) acenaphthene (BIAN)," Eur. J. Inorg. Chem. 2006, pp. 2985-2996.

Khusniyarov, M.M. et al., "Tuning the Oxidation Level, the Spin State, and the Degree of Electron Delocalization in Hom- and Heteroleptic Bis(α-diimine)iron Complexes," J. Am. Chem. Soc. 2009, v. 131, pp. 1208-1221.

Knisley, T.J. et al., "Low Temperature Growth of High Purity, Low Resistivity Copper Films by Atomic Layer Deposition," Chem. Mater. 2011, v. 23, pp. 4417-4419.

Knisley, T.J. et al., "Volatility and High Thermal Stability in Mid- to Late-First-Row Transition-Metal Dizazdienyl Complexes," Organometallics 2011, V. 30, pp. 5010-5017.

Kreisel, K.A. et al., "Synthesis, Characterization, and Electronic Structure of Diimine Complexes of Chromium," Inorganic Chem., v. 74, No. 12, (2008), pp. 5293-5303.

Kreisel, K.A. et al., "The Shortest Metal-Metal Bond Yet: Molecular and Electronic Structure of a Dinuclear Chromium Diazadiene Complex," J. Am. Chem. Soc. 2007, vo. 129, pp. 14162-14163.

Lim, B.S. et al., "Atomic layer deposition of transition metals," Nature Materials, v. 2, Nov. 2003, pp. 749-754.

Mac-Leod-Carey, D.A. et al., "Bix[2-(2,4-dioxopentan-3-ylidene-κO)-1-(4-methoxy-phenyl)hydrazinato-κN1] copper(II)," Acta Cryst. 2007, E63, pp. m670-m672.

Marten, J. et al., "3-(Arylhydrazono)pentane-2,4-diones and their Complexes with Copper(II) and Nickel(II)—Synthesis and Crystal Structures," Z. Anorg. Allg. Chem. 2005, v. 631, pp. 869-877.

Muresan, N. et al., "Bis(α-diimine)iron Complexes: Electronic Structure Determination by Spectroscopy and Broken Symmetry Density Functional Theoretical Calculations," Inorganic Chem., v. 47, No. 11, (2008), pp. 4579-4590.

Muresan, N. et al., "Bis(α-diimine)nickel Complexes: Molecular and Electronic Structure of Three Members of the Electron-Transfer Series [Ni(L)2]z (z=0, 1+, 2+) (L=2-Phenyl-1,4-bis(isopropyl)-1,4-diazabutadiene). A Combined Experimental and Theoretical Study," Inorganic Chem., v. 46, No. 13, (2007) pp. 5327-5337.

Muresan, N. et al., "Neutral (bis(1,4-diaza-1,3-butadiene)nickel complexes and their corresponding monocations: molecular and electronic structures. A combined experimental and density functional theoretical study," Dalton Trans., 2007, pp. 4390-4398.

Nassimbeni, L. et al., "The Crystal and Molecular Structure of the Bis-(5-ethyl-5-isoamylbarbiturato)bis(imidazole) Complex of Nickel(II)," Acta Cryst. (1974), B30, p. 2593-2602.

Pangani et al., "Coordination compounds of lanthanides with acetylhydrazine," Inorganica Chimca Acta, v. 94, issues 1-3, Feb. 1984, Abstract p. 79.

Pettinari, C. et al, "Copper and silver derivatives of scorpionates and related ligands," Polyhedron 23 (2004), pp. 451-469.

Popoff, N. et al., "Shifting from Ziegler-Natta to Phillips-Type Catalyst? A Simple and Safe Access to Reduced Titanium Systems for Ethylene Polymerization," Macromol. Rapid Commun. 2011, 32, pp. 1921-1924.

Rijnberg et al., "A Homologous Series of Homoleptic Zinc Bis(1,4-di-tert-butyl-1,4-diaza-1,3-butadiene) Complexes: Kx(Zn(t-BuNCHCHN-t-Bu)2 and (Zn(t-BuNCHCHN-t-Bu)2))(Otf)x (x=1,2)," Inorg. Chem. 1998, v. 37, pp. 56-63.

Robinson, M.A. et al., "Complexes Derived from Strong Field Ligands. XVII. Electronic Spectra of Octahedral Nickel(II) Complexes with Ligands of the α-Diimine and Closely Related Classes," Inorganic Chem., v. 2, No. 6, (1963), pp. 1178-1181.

Saito, T. et al., "1,4-Bis(trimethylsilyl)-,4-diaza-2,5-cyclohexadienes as Strong Salt-Free Reductants for Generating Low-Valent Early Transition Metals with Electron-Donating Ligands," J. Am. Chem. Soc. 2014, 136, pp. 5161-5170.

Svoboda, M. et al., "Bis(diazadien)metal(O)-Komplexe, III [1]1 Nickel(O)-bis(chelate) mit aliphatischen N-Substituenten," Z. Naturforsch. 86b, (1981), pp. 814-822—English Abstract.

Thompson, R.K. "Amidate Complexes of the Group 4 Metals," Synthesis, Reactivity, and Hydroaminiation Catalysis. Thesis, The University of British Columbia. http://hdl.handle.net/2429/1344. Available online Nov. 8, 2008, pp. 1-120.

Tsurugi, H. et al., "Carbon Radical Generation by D0 Tantalum Complexes with α-Diimine Ligands through Ligand-Centered Redox Processes," J. Am. Chem. Soc. 2011, 133, pp. 18673-18683.

Tsurugi, H. et al., "Salt-Free Reducing Reagent of Bis(trimethylsilyl)cyclohexadiene Mediates Multielectron Reduction of Chloride Complexes of W(VI) and W(IV)," J. Am. Chem. Soc. 2013, 135, pp. 5986-5989.

Vidjayacoumar et al., "Investigation of AlMe3, BEt3, and ZnEt2 as Co-Reagents for Low Temperature Copper Metal ALD/Pulsed-CVD," Chem. Mater. 2010, v. 22, pp. 4844-4853.

Yilmaz, F. et al., "Bis-(5,5'-diethylbarbiturato) Copper(II) and Cadmium(II Complexes with Ethylenediamine. Synthesis Crystal Structures, Spectroscopic and Thermal Characterization of cis-[Cu(barb)2(en) and {[Cd(barb)2(µ-en)]•2H2O}n," Z. Anorg. Allg. Chem. 2005, v. 631, pp. 1536-1540.

Non-Final Office Action mailed Apr. 7, 2014 in U.S. Appl. No. 13/319,793, filed Nov. 10, 2011, 7 pgs.

Non-Final Office Action mailed May 28, 2014 in U.S. Appl. No. 13/493,560, filed Jun. 11, 2012, 7 pgs.

Authors et al.: Disclosed Anonymously, IP.com Prior Art Database Technical Disclosure, IP.com No. IPCOM000173198D, Jul. 25, 2008.

Non-Final Office Action mailed Aug. 27, 2014 in U.S. Appl. No. 13/818,154, filed Feb. 21, 2013, 9 pgs.

Final Office Action Mailed Sep. 24, 2014 in U.S. Appl. No. 13/493,560 Filed Jun. 11, 2012, 23 pgs.

International Search Report, dated Oct. 27, 2014 in PCT/US2014/044669 filed Jun. 27, 2014, 3 pgs.

* cited by examiner

THERMALLY STABLE VOLATILE FILM PRECURSORS

CROSS-REFERENCE TO RELATED APPLICATION

This application is the U.S. national phase of PCT Appln. No. PCT/US2010/035080 filed May 17, 2010 which claims the benefit of U.S. provisional Ser. No. 61/178,734 filed May 15, 2009, the disclosures of which are incorporated in their entirety by reference herein.

TECHNICAL FIELD

The present invention relates to thermally stable volatile compounds for depositing thin films by thermally activated deposition processes, and, in particular, to thermally stable volatile compounds for depositing thin films by atomic layer deposition.

BACKGROUND

The growth of thin films is a central step in the fabrication of many functional materials and devices. While film growth efforts have been traditionally directed toward films greater than 100 nm, recent trends in several areas are calling for the growth of films ranging in thickness from a few atomic layers up to tens of nanometers.

As a significant example of this trend, the semiconductor industry has mandated a continuous reduction in microelectronics feature sizes from 65 nm in 2006 to 22 nm in 2016. This push toward smaller feature sizes requires controlled growth of films as thin as 1 nm. In addition to film growth on two-dimensional substrates such as etched silicon (Si) wafers, there is an increasing call to apply film growth techniques to nanoscale three-dimensional substrates such as nonparticles, nanowires, carbon nanotubes, and biomaterials such as viruses, proteins, and natural fibers. Films on these substrates can play protective, passivating, or other functional roles, or may reproduce the shape of interesting nanoscale entities. The coatings may be as thin as a few monolayers to achieve the desired properties.

Atomic layer deposition ("ALD") is a thin film deposition technique that addresses many of the current technological demands. In a typical ALD process, a substrate is contacted with a first chemical composition that modifies the substrate for a first predetermined period of time (a pulse). Such modification involves adsorption to the surface of the substrate, reaction with the surface of the substrate, or a combination of adsorption and reaction. A purging gas is introduced to remove any lingering first gaseous chemical composition in the vicinity of the substrate. A second gaseous chemical composition that reacts with the modified substrate surface is introduced for a second predetermined period of time into the vicinity of the substrate to form a portion of the thin film. A purging gas is subsequently introduced to remove any lingering second chemical composition in the vicinity of the substrate. These steps of contacting the substrate with the first chemical composition, purging, contacting the substrate with the second gaseous chemical composition, and purging are usually repeated a plurality of times until a film of desired thickness is coated onto the substrate. Although the prior art ALD processes work well, there is unfortunately only a limited number of chemical precursors having the requisite thermal stability, reactivity, and vapor pressure for ALD.

Accordingly, there is a need for thermally stable volatile precursors suitable for depositing thin films by atomic layer deposition.

SUMMARY OF THE INVENTION

The present invention solves one or more problems of the prior art by providing, in at least one embodiment, a precursor compound useful for depositing a thin film. The compound of this embodiment is described by formula 1:

$$M_x L_y \qquad 1$$

wherein
M is a metal;
x is 1 or 2;
y is an integer from 1 to 4;
L is $N(R_1R_2)$—$N$=$C(R_3)$—$O$ or $OC(R_4)$—$N(R_5)$;
$R_1$, $R_2$, $R_3$, $R_4$, and $R_5$ are each independently hydrogen, $C_{1-12}$ alkyl or $C_{6-12}$ aryl, $Si(R_6)_3$, or $Ge(R_6)_3$; and
$R_6$ is hydrogen, $C_{1-12}$ alkyl or $C_{6-12}$ aryl. Advantageously, the precursors of the present invention are useful in a number of coating processes, examples of which include, but are not limited to, ALD and chemical vapor deposition (CVD).

BRIEF DESCRIPTION OF THE DRAWINGS

Exemplary embodiments of the present invention will become more fully understood from the detailed description and the accompanying drawings, wherein.

DETAILED DESCRIPTION OF EXEMPLARY EMBODIMENTS

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The term "geometric isomer" as used herein means a chemical compound having the same molecular formula as another but a different geometric configuration. An example of a geometric isomer is when atoms or groups of atoms are attached in different spatial arrangements on either side of a double bond or other rigid bond or the orientation of a ligand about a metal or metal cluster.

The term "transition metal" as used herein means an element whose atom has an incomplete d sub-shell, or which can give rise to cations with an incomplete d sub-shell.

The term "thin film" as used herein means a coating on a substrate having a thickness less than about 0.5 microns. Typically, a thin film as used herein is a coating with a thickness less than about 500 nm. However, for many applications, a thin film as deposited by ALD is less than about 100 nm.

In an embodiment, a precursor compound for thin film deposition, and, in particular, for deposition of a thin film by atomic layer deposition (ALD) is provided. The precursor compound has formula 1:

$$M_xL_y \quad \quad 1$$

wherein
M is a transition metal;
x is 1 or 2;
y is an integer from 1 to 4;
L is $N(R_1R_2)-N=C(R_3)-O$ or $OC(R_4)-N(R_5)$;
$R_1$, $R_2$, $R_3$, $R_4$, and $R_5$ are each independently hydrogen, $C_{1-12}$ alkyl or $C_{6-12}$ aryl, $Si(R_6)_3$, or $Ge(R_6)_3$; and
$R_6$ is hydrogen, $C_{1-12}$ alkyl or $C_{6-12}$ aryl. Typically, the precursors of the present invention are characterized by having a useable vapor pressure at temperatures less than about 250° C. In a refinement, the precursor compounds have a vapor pressure above 0.05 Torr at a temperatures below 200° C.

In a refinement of the present embodiment, M is a metal in a 1+, 2+, 3+, or 4+ oxidation state. Typically, y is 1, 2, or 4 depending on the metal and its oxidation state. In some refinements, y is 2 when x is 1 and 4 when x is 2. In another refinement, y is 1 when M is a metal in the 1+ oxidation state. In still another refinement, y is 2 or 4 when M is a metal in the 2+ oxidation state. In yet another refinement, M is transition metal. Examples of useful transition metals, include, but are not limited to, Cu, Ni, Co, Cr, Mn, Fe, W, Mo, Ti, Zr, Hf, Rf, V, Nb, Ta, Re, Ru, Rh, Ir, Pd, Pt, and Au.

It should also be appreciated that the compounds having formula 1 may also include additional anionic or neutral ligands associated with the metal atom M depending on the oxidation state of M, the formal charge of M, and the method of preparing M. Moreover, in some variations, M has a formal charge of 1+, 2+, 3+ and 4+ while the ligand L has a formal charge of 1−. For example, the ligands in the formula 1 and in the structures below may be represented by the following structures if considered separate from the metal M:

while the Metal M may be considered as $M^{1+}$, $M^{2+}$, $M^{3+}$, $M^{4+}$. This understanding of representing chemical structures is well understood in the chemical arts and is completely analogous to representing sodium chloride as NaCl in which it is understood that each atom is charged. Chemists will readily recognize the nature of the charged states of the metal and ligands of the structures herein by applying well-known chemical structure techniques.

In yet another refinement of the present embodiment, $R_1$, $R_2$, $R_3$, $R_4$, and $R_5$ are each independently hydrogen, methyl, ethyl, n-propyl, isopropyl, n-butyl, t-butyl, or sec-butyl.

In a variation of the present embodiment, the precursor compound having formula 1 is also described by formula 2:

or geometric isomers thereof.

In the context of these compounds, geometric isomers include, but are not limited to, isomers in which the ligand atoms attaching to M are arranged in a tetrahedral configuration, a square planar configuration, or configurations intermediate between tetrahedral and square planar. In some geometric isomers, the O atoms attaching to M may be proximate (e.g., cis) or distant (e.g., trans). Examples for geometric isomers include, but are not limited to:

In a refinement of the compound described by formula 2, $R_1$, $R_2$, and $R_3$ are each independently hydrogen, methyl, ethyl, n-propyl, isopropyl, n-butyl, t-butyl, or sec-butyl. In another refinement of the compound described by formula 2, M is Cu, Ni, Co, Cr, Mn, or Fe. In yet another refinement of the compound described by formula 2, M is Cu, Ni, Co, or Cr.

In another variation of the present embodiment, the precursor compound having formula 1 is also described by formula 3:

3 or geometric isomers thereof.

In the context of these compounds, geometric isomers include, but are not limited to, isomers in which the ligand atoms attaching to M are arranged in a tetrahedral configuration, a square planar configuration, or configurations intermediate between tetrahedral and square planar. In some geometric isomers, the O atoms attaching to M may be proximate (e.g., cis) or distant (e.g., trans). In another refinement of the compound described by formula 3, M is Cu, Ni, Co, Cr, Mn, or Fe. In yet another refinement of the compound described by formula 3, M is Cu, Ni, Co, or Cr.

In another variation of the present embodiment, the precursor compound having formula 1 is also described by formula 4:

4 or geometric isomers thereof.

In the context of these compounds, geometric isomers include, but are not limited to, isomers in which the ligand atoms attaching to M are arranged in a tetrahedral configuration, a square planar configuration, or configurations intermediate between tetrahedral and square planar. In some geometric isomers, the O atoms attaching to M may be proximate (e.g., cis) or distant (e.g., trans). In a refinement of the compound described by formula 4, $R_1$, $R_2$, $R_3$ are each independently hydrogen, methyl, ethyl, n-propyl, isopropyl, n-butyl, t-butyl, or sec-butyl. In another refinement of the compound described by formula 4, M is Mn or Fe.

In another variation of the present embodiment, the precursor compound having formula 1 is also described by formula 5:

5 or geometric isomers thereof.

In the context of these compounds, geometric isomers include, but are not limited to, isomers in which the ligand atoms attaching to M are arranged in a tetrahedral configuration, a square planar configuration, or configurations intermediate between tetrahedral and square planar. In some geometric isomers, the O atoms from different ligands attaching to M may be proximate (e.g., cis) or distant (e.g., trans). Examples for geometric isomers include, but are not limited to:

In a refinement of the compound described by formula 5, $R_4$ and $R_5$ are each independently hydrogen, methyl, ethyl, n-propyl, isopropyl, n-butyl, t-butyl, or sec-butyl. In another refinement of the compound described by formula 5, M is Cu, Ni, Co, Cr, Mn, or Fe. In yet another refinement of the compound described by formula 5, M is Cu, Ni, Co, or Cr.

In another variation of the present embodiment, the precursor compound having formula 1 is also described by formula 6:

6 or geometric isomers thereof,

In the context of these compounds, geometric isomers include, but are not limited to, isomers in which the ligand atoms attaching to M are so that the O atoms attaching to M are proximate (e.g., cis) or distant (e.g., trans). Examples of geometric isomers for compounds having formula 6 include, but are not limited to:

In a refinement of the compound described by formula 6, $R_4$ and $R_5$ are each independently hydrogen, methyl, ethyl, n-propyl, isopropyl, n-butyl, t-butyl, iso-butyl or sec-butyl. The ----- between M is absent, a single bond, or a multiple bond. In another refinement of the compound described by formula 6, M is Cu, Ni, Co, Cr, Mn, or Fe. In yet another refinement of the compound described by formula 6, M is Cu, Ni, Co, or Cr.

In another variation of the present embodiment, the precursor compound having formula 1 is also described by formula 7:

7 or geometric isomers thereof;

In the context of these compounds, geometric isomers include, but are not limited to, isomers in which the ligand atoms attaching to M are so that the O atoms attaching to M are proximate (e.g., cis) or distant (e.g., trans). Examples of geometric isomers for compounds having formula 7 include, but are not limited to:

-continued

In a refinement of the compound described by formula 7, $R_4$ and $R_5$ are each independently hydrogen, methyl, ethyl, n-propyl, isopropyl, n-butyl, t-butyl, iso-butyl or sec-butyl. The between M is absent, a single bond, or a multiple bond. In another refinement of the compound described by formula 7, M is Cu, Ni, Co, or Cr.

Figure 1:
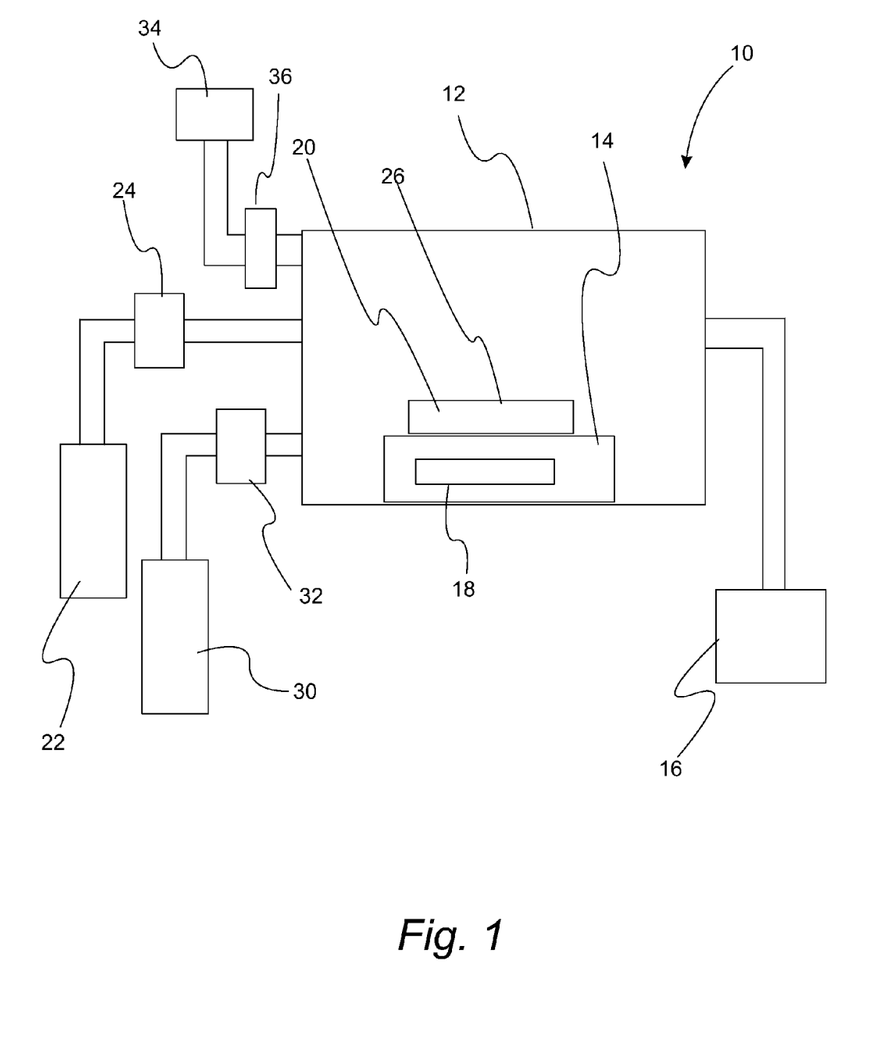
FIG. 1 is a schematic illustration of an atomic layer deposition system.

In another embodiment of the present embodiment, a method for depositing a thin film on a surface of a substrate using the precursor compounds set forth above is provided. Deposition system 10 includes reaction chamber 12, substrate holder 14, and vacuum pump 16. Typically, the substrate is heated via heater 18. The method has a deposition cycle comprising contacting substrate 20 with a vapor of a metal-containing compound described by any of formulae 1-7. In particular, the vapor is introduced from precursor source 22 into reaction chamber 12 for a predetermined pulse time. The pulse time is controlled via control valve 24. At least a portion of the vapor of the metal-containing compound modifies (e.g, adsorbs or reacts with) substrate surface 26 to form a modified surface. The method further comprises contacting the modified surface with a vapor of an activating compound from activating compound source 30 for a predetermined pulse time. The pulse time is controlled via control valve 32. The activating compound causes the metal-containing compound to react and form at least a portion of the thin film on the surface of the substrate. The reduced pressure of chamber 12 is maintained by vacuum pump 16.

In a variation of the present embodiment, the method further comprises removing at least a portion of the vapor of the metal containing compound that is lingering in the gas phase (i.e., has not adsorbed or reacted with the substrate) from the vicinity of the substrate before introducing the vapor of the activating compound and removing at least a portion of the vapor of the activating compound from the vicinity of the substrate. The metal-containing compound and the activating compound are removed in purging steps by introducing a purge gas from purge source 34 into reaction chamber 12 for a predetermined purge time. The purge time is controlled by control valve 36.

In another variation, the method further includes at least one additional deposition cycle comprising sequentially contacting the substrate with the vapor of a metal-containing compound (formulae 1-7) and then the vapor of an activating compound. In some refinements, the substrate is contacted for a plurality of additional deposition cycles. For example, the substrate may be contacted with from 1 to several thousand deposition cycles depending on the thickness of the film desired.

In another variation, the activating compound is a reducing agent. In this variation, the resulting thin film is a metallic film. Examples of useful reducing agents include, but are not limited to, molecular hydrogen, atomic hydrogen, silane, disilane, organosilanes, compounds containing Si—H bonds, germane, organogermanes, compounds containing Ge—H bonds, stannane, compounds containing Sn—H bonds, other metal hydride compounds, formic acid, glyoxalic acid, oxalic acid, other carboxylic acids, diborane, compounds containing B—H bonds, hydrazine, carbon-substituted hydrazines, formalin, formaldehyde, organic alcohols, organoaluminum compounds, organozinc compounds, other organometallic compounds, plasma-activated versions of the above compounds.

In still another variation, the activating compound is an oxidizing agent with the resulting thin film being a metal oxide. Examples of useful oxidizing agents include, but are not limited to, water, ozone, molecular oxygen, atomic oxygen, organic alcohols, hydrogen peroxide, organic hydroperoxides, organic peroxides, nitrous oxide, plasma-activated versions of the above compounds.

During film formation by the method of the present embodiment, the substrate temperature will be at a temperature suitable to the properties of the chemical precursor(s) and film to be formed. In a refinement of the method, the substrate is set to a temperature from about 0 to 1000° C. In another refinement of the method, the substrate has a temperature from about 50 to 450° C. In another refinement of the method, the substrate has a temperature from about 100 to 250° C. In still another refinement of the method, the substrate has a temperature from about 150 to 400° C. In another refinement of the method, the substrate has a temperature from about 200 to 300° C.

Similarly, the pressure during film formation is set at a value suitable to the properties of the chemical precursors and film to be formed. In one refinement, the pressure is from about $10^{-6}$ Torr to about 760 Torr. In another refinement, the pressure is from about 0.1 millitorr to about 10 Torr. In still another refinement, the pressure is from about 1 to about 100 millitorr. In yet another refinement, the pressure is from about 1 to 20 millitorr.

Pulse times and purge times also depend on the properties of the chemical precursors and the geometric shape of the substrates. Thin film growth on flat substrates uses short pulse and purge times, but pulse and purge times in ALD growth on 3-dimensional substrates can be very long. Therefore, in one refinement, pulse times and purge times are each independently from about 0.0001 to 200 seconds. In another refinement, pulse and purge times are each independently from about 0.1 to about 10 seconds.

The following examples illustrate the various embodiments of the present invention. Those skilled in the art will recognize many variations that are within the spirit of the present invention and scope of the claims.

1. Preparation of Mononuclear and Dinuclear Copper(II) Complexes Containing Amidate Ligands.

1.1 Synthesis of Ligands.

The secondary amide pro-ligands N-tert-butylpivalamide ($L^{tBu,tBu}H$), N-tert-butylisobutyramide ($L^{iPr,tBu}H$), N-tert-butylpropionamide ($L^{Et,tBu}H$), N-tert-butylacetamide ($L^{Me,tBu}H$), N-isopropylpivalamide ($L^{tBu,iPr}H$), N-isopropylisobutyramide ($L^{iPr,iPr}H$), N-isopropylpropionamide ($L^{Et,iPr}H$), N-isopropylacetamide ($L^{Me,iPr}H$), N-isopropylbenzamide ($L^{Ph,iPr}H$), and N-(2,4-dimethylpentan-3-yl)pivalamide ($L^{tBu,CHiPr2}H$) were prepared according to literature procedures using commercially available carboxylic acid chlorides and primary amines in the presence of triethylamine as a base. A few modifications to the method were made for ease of synthesis and to increase the yield (eq 1). The byproduct, triethylamine hydrochloride, is insoluble in diethylether ($Et_2O$) and is removed by suction filtration. The ligand 2,2,3,3,3-pentafluoro-N-isopropylpropanamide ($L^{C2F5,iPr}H$) was prepared by following a similar method using a commercially available corresponding acid-anhydride in place of the acid chloride and the byproduct was removed by solvent extraction of the crude product with water (eq 2). The crude products present after the removal of the volatile components by rotary evaporation were sublimed at 50-70° C./0.05 Torr to afford crystalline products in greater than 90% yield, except $L^{Me,iPr}H$, which is a liquid isolated by vacuum distillation at 65° C./0.05 Torr in 95% yield. Lithium and potassium salts of the ligands were prepared in situ by treating the protonated ligands with the appropriate alkyl lithium reagent or potassium hydride in tetrahydrofuran prior to every reaction.

(1)

(2)

1.2 Synthesis of Copper Complexes.

Treatment of anhydrous copper(II) chloride, $CuCl_2$, or its TMEDA adduct, $CuCl_2(TMEDA)$, with two equivalents of the appropriate potassium-amidate salts prepared in situ in tetrahydrofuran afforded dinuclear or mononuclear bis-amidato copper(II) complexes in moderate to high yields (eq 3). Both anhydrous $CuCl_2$ and $CuCl_2(TMEDA)$ are insoluble in tetrahydrofuran at ambient temperatures and display similar reactivity in most cases. The exceptions are that $[Cu(MeC(O)NtBu)_2]_2$ (10) can only be made using $CuCl_2(TMEDA)$, while $[Cu((C_2F_5)C(O)NiPr)_2]_2$ (15) is only obtained with $CuCl_2$. Treatment of anhydrous $CuCl_2$ or $CuCl_2(TMEDA)$ with $L^{tBu,tBu}K$ did not afford any isolable compound.

(3)

-continued

8, R = iPr, R' = tBu, 71%
9, R = Et, R' = tBu, 68%
10, R = Me, R' = tBu, 63%*
11, R = tBu, R' = iPr, 73%
12, R = iPr, R' = iPr, 80%
13, R = Me, R' = iPr, 75%
14, R = Ph, R' = iPr, 61%
15, R = $C_2F_5$, R' = iPr, 52%**

16, 73%

\* Only with $CuCl_2$(TMEDA)
\*\* Only with $CuCl_2$

Treatment of $CuCl_2$ or $CuCl_2$(TMEDA) with two equivalents of $L^{iPr,tBu}K$ in tetrahydrofuran at ambient temperature afforded the dinuclear bis-amidate complex $[Cu(L^{iPr,tBu})_2]_2$ (8) in 71% yield upon sublimation at 88° C. and 0.05 Torr (eq 8). Similar treatment of $CuCl_2$ or $CuCl_2$(TMEDA) with two equivalents of $L^{Et,tBu}K$, $L^{tBu,iPr}K$, $L^{iPr,iPr}K$, $L^{Me,iPr}K$, $L^{Ph,iPr}K$ or $L^{tBu,CHiPr2}K$ in tetrahydrofuran at ambient temperature afforded $[Cu(L^{Et,tBu})_2]_2$ (9, 68%), $[Cu(L^{tBu,iPr})_2]_2$ (11, 73%), $[Cu(L^{iPr,iPr})_2]^2$ (12, 80%), $[Cu(L^{Me,iPr})_2]_2$ (13, 75%), $[Cu(L^{Ph,iPr})_2]_2$ (14, 61%), and $Cu(L^{tBu,CHiPr2})_2$ (16, 73%), respectively. $[Cu(L^{Me,tBu})_2]_2$ (10) was made in 63% yield by treating $CuCl_2$(TMEDA) with two equivalents of $L^{Me,tBu}K$, while $[Cu(L^{C2F5,iPr})_2]_2$ (15) was made in 52% yield by treating $CuCl_2$ with two equivalents of $L^{C2F5,iPr}K$ (eq 3). Pure crystalline solids of complexes 8-12 and 15 were obtained by vacuum sublimation at 88, 86, 95, 77, 98, and 75° C. at 0.05 Torr, respectively. Complexes 13, 14, and 16 do not sublime and were purified by recrystallization from hexane solutions at −20° C. Complexes 10-12 and 15 undergo concomitant decomposition while subliming, thus leading to lower sublimation yields. Complexes 8-11 and 15 can also be crystallized from hexane solution at −20° C., but the extreme solubility of compound 12 in hexane and pentane makes it impossible to isolate it from solution. Crystalline solids of 8-11 and 16 are dark blue in color while 12 and 13 are wine-red and 14 and 15 are purple. The structural assignments for 8-16 are based upon spectral and analytical data. In addition, X-ray crystal structure determinations were carried out for 8-11, 13, 14, and 16.

1.3 Volatility and Thermal Stability Study.

The volatilities of 8 and 9 were evaluated by preparative sublimation experiments. About 0.5 g of previously sublimed samples of 8 and 9 were re-sublimed at 90 and 88° C./0.05 Torr, respectively, and the percent recoveries and percent non-volatile residues were reported as 85%, 1.4% for 8 and 78%, 4.3% for 9, respectively. In the decomposition study, a few milligrams of each sample were sealed under the exclusion of oxygen and moisture in argon-filled capillary tubes and heated at 5° C./min from 25 to 175° C. Samples were visually monitored for discoloration and change of texture and 8 decomposed upon melting at 155° C. while 9 decomposed at 120° C. within 15 minutes.

1.4 Experimental

Preparation of N-tert-butylpivalamide ($L^{tBu,tBu}H$).

A 1 L three-necked round-bottomed flask was charged with diethylether (500 mL), tert-butylamine (11.3 mL, 105 mmol), and triethylamine (14.9 mL, 105 mmol). To this vigorously stirred solution at 0° C. was slowly added pivaloyl chloride (8.9 mL, 100 mmol) and the resultant white slurry was stirred for 18 h at ambient temperature. This slurry was then filtered with a water aspirator pump and the volatile components of the filtrate were removed under reduced pressure. The resultant crystalline solid was sublimed at 55° C./0.05 Torr to afford $L^{tBu,tBu}H$ as white crystals (15.41 g, 98%): mp 116-118° C.

Preparation of N-tert-butylisobutyramide ($L^{iPr,tBu}H$).

In a fashion similar to the preparation of $L^{tBu,tBu}H$, treatment of tert-butylamine (11.3 mL, 105 mmol) and triethylamine (14.9 mL, 105 mmol) with isobutyryl chloride (10.8 mL, 100 mmol) afforded $L^{iPr,tBu}H$ as white crystalline solid (13.75 g, 96%) upon sublimation at 55° C./0.05 Torr: mp 117-119° C.

Preparation of N-tert-butylpropionamide ($L^{Et,tBu}H$).

In a fashion similar to the preparation of $L^{tBu,tBu}H$, treatment of tert-butylamine (11.3 mL, 105 mmol) and triethylamine (14.9 mL, 105 mmol) with propionyl chloride (8.9 mL, 100 mmol) afforded $L^{Et,tBu}H$ as white crystalline solid (12.27 g, 95%) upon sublimation at 55° C./0.05 Torr: mp 90-92° C.

Preparation of N-tert-butylacetamide ($L^{Me,tBu}H$).

In a fashion similar to the preparation of $L^{tBu,tBu}H$, treatment of tert-butylamine (11.3 mL, 105 mmol) and triethylamine (14.9 mL, 105 mmol) with acetyl chloride (7.25 mL, 100 mmol) afforded $L^{Me,tBu}H$ as white crystalline solid (11.17 g, 97%) upon sublimation at 55° C./0.05 Torr: mp 97-99° C.

Preparation of N-isopropylpivalamide ($L^{tBu,iPr}H$).

In a fashion similar to the preparation of $L^{tBu,tBu}H$, treatment of isopropylamine (9.0 mL, 105 mmol) and triethylamine (14.9 mL, 105 mmol) with pivaloyl chloride (8.9 mL, 100 mmol) afforded $L^{tBu,iPr}H$ as white crystalline solid (13.75 g, 96%) upon sublimation at 55° C./0.05 Torr: mp 106-108° C.

Preparation of N-isopropylisobutyramide ($L^{iPr,iPr}H$).

In a fashion similar to the preparation of $L^{tBu,tBu}H$, treatment of isopropylamine (9.0 mL, 105 mmol) and triethylamine (14.9 mL, 105 mmol) with isobutyryl chloride (10.8 mL, 100 mmol) afforded $L^{iPr,iPr}H$ as white crystalline solid (12.14 g, 94%) upon sublimation at 55° C./0.05 Torr: mp 104-106° C.

Preparation of N-isopropylpropionamide ($L^{Et,iPr}H$).

In a fashion similar to the preparation of $L^{tBu,tBu}H$, treatment of isopropylamine (9.0 mL, 105 mmol) and triethylamine (14.9 mL, 105 mmol) with propionyl chloride (8.9 mL, 100 mmol) afforded $L^{Et,iPr}H$ as white crystalline solid (10.48 g, 91%) upon crystallization from hexane followed by sublimation at 50° C./0.05 Torr: mp 47-49° C.

Preparation of N-isopropylacetamide ($L^{Me,iPr}H$).

In a fashion similar to the preparation of $L^{tBu,tBu}H$, treatment of isopropylamine (9.0 mL, 105 mmol) and triethylamine (14.9 mL, 105 mmol) with acetyl chloride (7.25 mL, 100 mmol) afforded $L^{Me,iPr}H$ as colorless liquid (9.61 g, 95%) upon distillation at 65° C./0.05 Torr.

Preparation of N-isopropylbenzamide ($L^{Ph,iPr}H$).

In a fashion similar to the preparation of $L^{tBu,tBu}H$, treatment of isopropylamine (9.0 mL, 105 mmol) and triethylamine (14.9 mL, 105 mmol) with benzoyl chloride (11.72 mL, 100 mmol) afforded $L^{Ph,iPr}H$ as white crystalline solid (15.02 g, 92%) upon crystallization of the crude product from Et$_2$O at −20° C. followed by sublimation at 70° C./0.05 Torr: mp 101-103° C.

Preparation of 2,2,3,3,3-pentafluoro-N-isopropylpropanamide ($L^{C2F5,iPr}H$).

A 500 mL three-necked round-bottomed flask was charged with diethyl ether (250 mL), isopropylamine (9.0 mL, 105 mmol), and triethylamine (14.9 mL, 105 mmol). To this vigorously stirred solution at 0° C. was slowly added 2,2,3,3,3-pentafluoropropanoic anhydride (20.1 mL, 100 mmol) and the resultant pale yellow clear solution was stirred for 12 h at ambient temperature. This solution was extracted with water (5×100 mL) and the Et$_2$O layer was separated and then dried over anhydrous MgSO$_4$. The volatile components were removed under reduced pressure and the pale yellow solid was sublimed at 55° C./0.05 Torr to afford $L^{C2F5,iPr}H$ as white crystalline solid (18.46 g, 90%): mp 54-56° C.

Preparation of N-(2,4-dimethylpentan-3-yl)pivalamide ($L^{tBu,CHiPr2}H$).

In a fashion similar to the preparation of $L^{tBu,tBu}H$, treatment of 2,4-dimethylpentan-3-amine (14.0 mL, 100 mmol) and triethylamine (14.9 mL, 105 mmol) with pivaloyl chloride (8.9 mL, 100 mmol) afforded $L^{tBu,CHiPr2}H$ as white crystalline solid (19.53 g, 98%) upon sublimation at 65° C./0.05 Torr: mp 107-109° C.

Preparation of $[Cu(L^{iPr,tBu})_2]_2$ (8).

A 100 mL Schlenk flask, equipped with a magnetic stir bar and a rubber septum, was charged with $L^{iPr,tBu}H$ (0.627 g, 4.38 mmol) and tetrahydrofuran (30 mL). To this stirred solution at ambient temperature was slowly added potassium hydride (0.193 g, 4.82 mmol) and the resultant colorless solution was stirred for 5 h. This solution was then slowly added over 15 min to a stirred suspension of anhydrous copper(II) chloride (0.300 g, 2.19 mmol) in tetrahydrofuran (10 mL). The resultant blue solution was stirred for an additional 45 min at ambient temperature. The volatile components were then removed under reduced pressure and the resultant blue solid was dissolved in hexane (40 mL). The solution was filtered through a 1-cm pad of Celite on a coarse glass frit, and a blue crystalline solid remained upon removal of hexane under reduced pressure. This solid was sublimed at 88° C./0.05 Torr to afford 1 as blue crystals (0.539 g, 71%): mp 153-155° C.

Preparation of $[Cu(L^{Et,tBu})_2]_2$ (9).

In a fashion similar to the preparation of 1, treatment of anhydrous copper(II) chloride (0.300 g, 2.19 mmol) in tetrahydrofuran (10 mL) with $L^{Et,tBu}K$ (prepared from $L^{Et,tBu}H$ (0.566 g, 4.38 mmol) and potassium hydride (0.193 g, 4.82 mmol) in tetrahydrofuran (30 mL)) for a total of 1 h at ambient temperature afforded 2 (0.328 g, 47%) as blue crystals from sublimation at 86° C./0.05 Torr: mp 106-109° C.

Preparation of $[Cu(L^{Me,tBu})_2]_2$ (10).

A 100 mL Schlenk flask, equipped with a magnetic stir bar and a rubber septum, was charged with anhydrous CuCl$_2$ (TMEDA) (0.502 g, 2.00 mmol) and tetrahydrofuran (20 mL). To this stirred suspension at ambient temperature was slowly added $L^{Me,tBu}K$, which was prepared in situ from $L^{Me,tBu}H$ (0.461 g, 4.00 mmol) and potassium hydride (0.176 g, 4.39 mmol) in tetrahydrofuran (30 mL). The resultant blue solution was stirred an additional 2 h at ambient temperature. The volatile components were then removed under reduced pressure and the resultant blue solid was dissolved in toluene (30 mL). The solution was filtered through a 1-cm pad of Celite on a coarse glass frit, and a blue solid remained upon the removal of toluene under reduced pressure. This solid was sublimed at 95° C./0.05 Torr to afford 10 as blue crystals (0.182 g, 31%): mp 134-138° C.

Preparation of $[Cu(L^{tBu,iPr})_2]_2$ (11).

In a fashion similar to the preparation of 8, treatment of anhydrous copper(II) chloride (0.300 g, 2.19 mmol) in tetrahydrofuran (10 mL) with $L^{tBu,iPr}K$ (prepared from $L^{tBu,iPr}H$ (0.627 g, 4.38 mmol) and potassium hydride (0.193 g, 4.82 mmol) in tetrahydrofuran (30 mL)) for a total of 30 min at ambient temperature afforded 11 (0.162 g, 21%) as blue crystals from sublimation at 77° C./0.05 Torr: mp 120-123° C.

Preparation of $[Cu(L^{iPr,iPr})_2]_2$ (12).

In a fashion similar to the preparation of 8, treatment of anhydrous copper(II) chloride (0.300 g, 2.19 mmol) in tetrahydrofuran (10 mL) with $L^{iPr,iPr}K$ (prepared from $L^{iPr,iPr}H$ (0.566 g, 4.38 mmol) and potassium hydride (0.193 g, 4.82 mmol) in tetrahydrofuran (30 mL)) for a total of 2 h at ambient temperature afforded 12 (0.210 g, 33%) as wine-red crystals from sublimation at 98° C./0.05 Torr: mp 138-141° C.

Preparation of $[Cu(L^{Me,iPr})_2]_2$ (13).

In a fashion similar to the preparation of 8, treatment of anhydrous copper(II) chloride (0.300 g, 2.19 mmol) in tetrahydrofuran (10 mL) with $L^{Me,iPr}K$ (prepared from $L^{Me,iPr}H$ (0.443 g, 4.38 mmol) and potassium hydride (0.193 g, 4.82 mmol) in tetrahydrofuran (30 mL)) for a total of 2 h at ambient temperature afforded 13 (0.431 g, 75%) as wine-red crystals after crystallization from hexane: mp 96-99° C.

Preparation of $[Cu(L^{Ph,iPr})_2]_2$ (14).

In a fashion similar to the preparation of 8, treatment of anhydrous copper(II) chloride (0.300 g, 2.19 mmol) in tetrahydrofuran (10 mL) with $L^{Ph,iPr}K$ (prepared from $L^{Ph,iPr}H$ (0.714 g, 4.38 mmol) and potassium hydride (0.193 g, 4.82 mmol) in tetrahydrofuran (30 mL)) for a total of 1 h at ambient temperature afforded 14 (0.517 g, 61%) as purple crystals after crystallization from 50 mL of hexane: mp 162-165° C.

Preparation of [Cu(LC2F5,iPr)2]2 (15).

In a fashion similar to the preparation of 8, treatment of anhydrous copper(II) chloride (0.300 g, 2.19 mmol) in tetrahydrofuran (10 mL) with $L^{C2F5,iPr}K$ (prepared from $L^{C2F5,iPr}H$ (0.898 g, 4.38 mmol) and potassium hydride (0.193 g, 4.82 mmol) in tetrahydrofuran (30 mL)) for a total of 2 h at ambient temperature afforded 15 (0.536 g, 52%) as purple crystals from sublimation at 75° C./0.05 Torr: mp 201-203° C.

Preparation of $Cu(L^{tBu,CHiPr2})_2$ (16).

In a fashion similar to the preparation of 8, treatment of anhydrous copper(II) chloride (0.300 g, 2.19 mmol) in tetrahydrofuran (10 mL) with $L^{tBu,CHiPr2}K$ (prepared from $L^{tBu,CHiPr2}H$ (0.872 g, 4.38 mmol) and potassium hydride (0.193 g, 4.82 mmol) in tetrahydrofuran (30 mL)) for a total of 5 h at ambient temperature afforded 16 (0.752 g, 73%) as blue crystals after crystallization from hexane: mp 109-112° C.

2. Preparation of Monomeric and Dimeric Chromium(II) and Chromium(III) Complexes Containing Amidate Ligands

2.1 Synthesis of Chromium(II) Complexes.

The synthesis of secondary amide proligands was described above in section 1. Salt metathesis reactions were achieved by the use of the potassium salts of the amides (prepared in situ from the corresponding amide and potassium hydride) and simultaneous exploitation of the 4-tBupy adduct of CrCl$_2$ in THF solution. In the course of the reaction, 4-tBupy provides sufficient solubility of CrCl$_2$ in tetrahydrofuran as well as preventing oligomerization reactions by saturating the open coordination sites. Pretreatment of anhydrous

CrCl$_2$ with three equivalents of 4-tBupy in tetrahydrofuran followed by the addition of two equivalents of L$^{tBu,tBu}$K at ambient temperature afforded the monomeric bis-amidate complex Cr(L$^{tBu,tBu}$)$_2$(4-tBupy)$_3$ (17) as dark green crystals in 54% yield upon hexane workup (eq 4). Subsequent sublimation of 17 at 120° C. and 0.05 Torr afforded [Cr(L$^{tBu,tBu}$)$_2$]$_2$ (18) as orange crystals in 68% yield with the simultaneous loss of 4-tBupy (eq 4). Similar treatments of CrCl$_2$ with two equivalents of L$^{iPr,tBu}$K, L$^{Me,tBu}$K, or L$^{tBu,iPr}$K in the presence of 4-tBupy in tetrahydrofuran solution at ambient temperature and subsequent sublimation of the crude products (without hexane workup) afforded [Cr(L$^{iPr,tBu}$)$_2$]$_2$ (19, 48%), [Cr(L$^{Me,tBu}$)$_2$]$_2$ (20, 82%), or [Cr(L$^{tBu,iPr}$)$_2$]$_2$ (21, 48%), respectively, as yellow to orange crystals (eq 5). All reaction manipulations and the crystalline products 17 and 18 were handled under inert atmosphere; however, 19-21 as isolated after sublimation are air stable indefinitely.

Crystals of 18-20 suitable for X-ray diffraction experiments were obtained by recrystalizing the sublimed products from either pentane or hexane solution at −20° C. The structural assignments for 17-21 are based upon spectral and analytical data. In addition, X-ray crystal structure determinations were carried out for 17-20. Several attempts were made to get a higher precision structure determination for 21, but only a low precision X-ray crystal structure determination was achieved, which provided an unambiguous identification for a dimeric structure with four bridging μ-η$^1$:η$^1$-L$^{tBu,iPr}$ ligands. The spectra of 18-21 in benzene-d$_6$ consist of sharp signals for the ligand substituents, due to the diamagnetic nature of the complexes arising from complete antiferromagnetic coupling of the dinuclear Cr$_2^{4+}$ cores. In the infrared spectrum of 18, two carbonyl stretching frequencies were observed for the two different ligand coordinations, as (4)

17 54%

18, 68%

(5)

19, R = iPr, R' = tBu, 48%
20, R = Me, R' = tBu, 82%
21, R = tBu, R' = iPr, 48% expected. The other dimers 19-21 each showed one carbonyl stretching frequency, which is consistent with their structure.

2.2 Synthesis of Chromium(III) Complexes.

Treatment of anhydrous chromium(III) chloride with three equivalents of $L^{iPr,tBu}$Li, $L^{Me,tBu}$Li, $L^{iPr,iPr}$Li, or $L^{Me,iPr}$Li (prepared in situ from the corresponding amide and methyllithium) in tetrahydrofuran afforded 22-25 as dark purple crystals or viscous liquids in good to moderate yields (eq 6). Analytically pure crystals of 22 and 23 were isolated by sublimation at 92 and 90° C./0.05 Torr, respectively, and the viscous liquid products 24 and 25 were isolated by short-path vacuum distillation in a Kugelrohr apparatus at 105° C./0.05 Torr.

22, R = iPr, R' = tBu, 70%
23, R = Me, R' = tBu, 66%
24, R = iPr, R' = iPr, 54%
25, R = Me, R' = iPr, 43%

The structural assignments for 22-25 are based upon spectral and analytical data. In addition, X-ray crystal structure determinations were carried out for the crystalline compounds, 22 and 23. Compound 22 has a mononuclear structure. A low precision X-ray crystal structure was obtained for 23 due to the poor quality of crystals, and provides an unambiguous identification that it has a monomeric structure similar to that of 22.

2.3 Volatility and Thermal Stability Study 2.3.1 Dinuclear Chromium(II) Compounds.

The initial screening for the thermal stability of compounds 18-21 was performed by melting point and decomposition point determinations. Compounds 19-21 were selected and further evaluated by preparative sublimation studies and thermogravimetric analysis (TGA) to establish their suitability as potential ALD precursors. The volatility and thermal decomposition data for 19-21 are summarized in Table 1. In the thermal stability study, a few milligrams of each sample were sealed under the exclusion of oxygen and moisture in argon-filled capillary tubes and heated at 5° C./min from 25 to 400° C. Samples were visually monitored for discoloration and change of texture, and the thermal stability was decisively evaluated by NMR experiments of the samples heated slightly below their visual decomposition points. Samples 18-21 decomposed at 203, 347, 305, and 350° C., respectively. Compounds 18, 19, and 21 decompose upon melting and 20 melts at 247-250° C. while its decomposition occurs at 305° C. Orange colored crystals of 19 turn slightly brown between 265 to 325° C., and yellow colored crystals of 21 turn orange about 275° C. although the crystals remain intact and return to their original crystal color upon cooling back to 25° C. Another set of samples of 19-21 were heated at a rate of 5° C./min up to 340, 300, and 340° C., respectively, and the end temperatures were maintained for two minutes. The $^1$H NMR spectra of these heat-treated samples of 19-21 was identical to the corresponding $^1$H NMR spectra of the pure samples. The clear absence of free ligand signals or paramagnetic artifacts from paramagnetic chromium residues established the thermal stability of 19-21 with utmost certainty.

TABLE 1

Preparative Sublimation Data and Decomposition Temperatures for 19-21.[a]

| Compound | Preparative Sublimation Temperature (° C./0.05 Torr) | % Recovery | % Residue | Decomposition Temperature (° C.) |
|---|---|---|---|---|
| 19 | 140 | 98.4 | 0.5 | 347 |
| 20 | 125 | 99.6 | 0.2 | 305 |
| 21 | 145 | 99.1 | 0.5 | 350 |

[a]All preparative sublimations were carried out on a 0.5-1.0 g scale and were completed in less than 3 hours at temperatures 20° C. higher than their sublimation temperatures.

Figure 2:
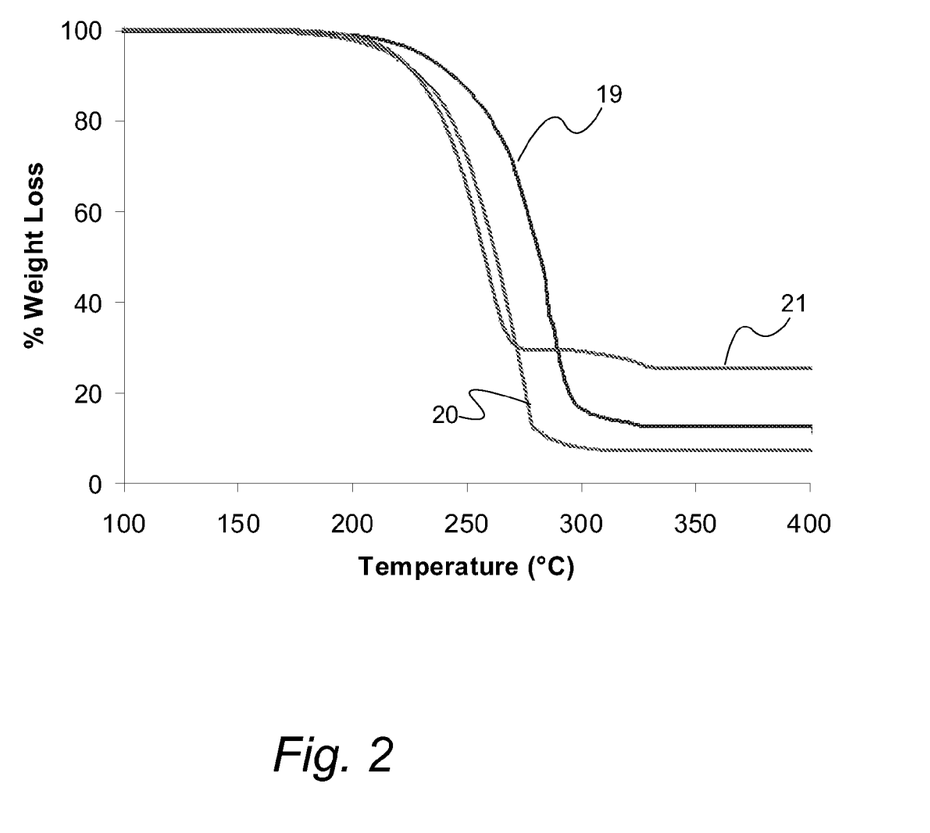
FIG. 2 provides TGA traces for compounds 19-21 from 100 to 400° C. at 10° C./min.

In preparative sublimation studies, samples of 19-21 at temperatures 10-20° C. higher than their experimental sublimation temperatures were complete in less than 3 hours. Nonvolatile residues for all three compounds are ≤0.5%, with nearly quantitative sublimation recoveries (Table 1). Complex 20 is the most volatile among 19-21 and a 0.8 g sample sublimed at 125° C./0.05 Torr within two hours with sublimation recovery of 99.6% and a nonvolatile residue of 0.15%. The sublimation behavior of 19 and 21 are similar and only slightly different from 20, reflecting the identical molar mass of 19 and 21 (Table 1). The TGA traces for 19-21 are shown in FIG. 2. All compounds show single step sublimations. Complex 20 sublimes from 153-282° C. with a residue of 7.3%, which was the best sublimation behavior among the three complexes. The sublimation temperature windows and corresponding residues of 19 and 21 are 148-300 and 180-276° C., and 12.8 and 25.5%, respectively. It is important to note that the sublimation of 19-21 at atmospheric pressure in TGA ceases at much lower temperatures than their decomposition temperatures in the condensed phase. This could be a consequence of the exposure of the samples to air during sample preparation for TGA, whereas the samples were kept under argon throughout the melting point decomposition studies.

2.3.2 Mononuclear Chromium(III) Compounds.

Figure 3:
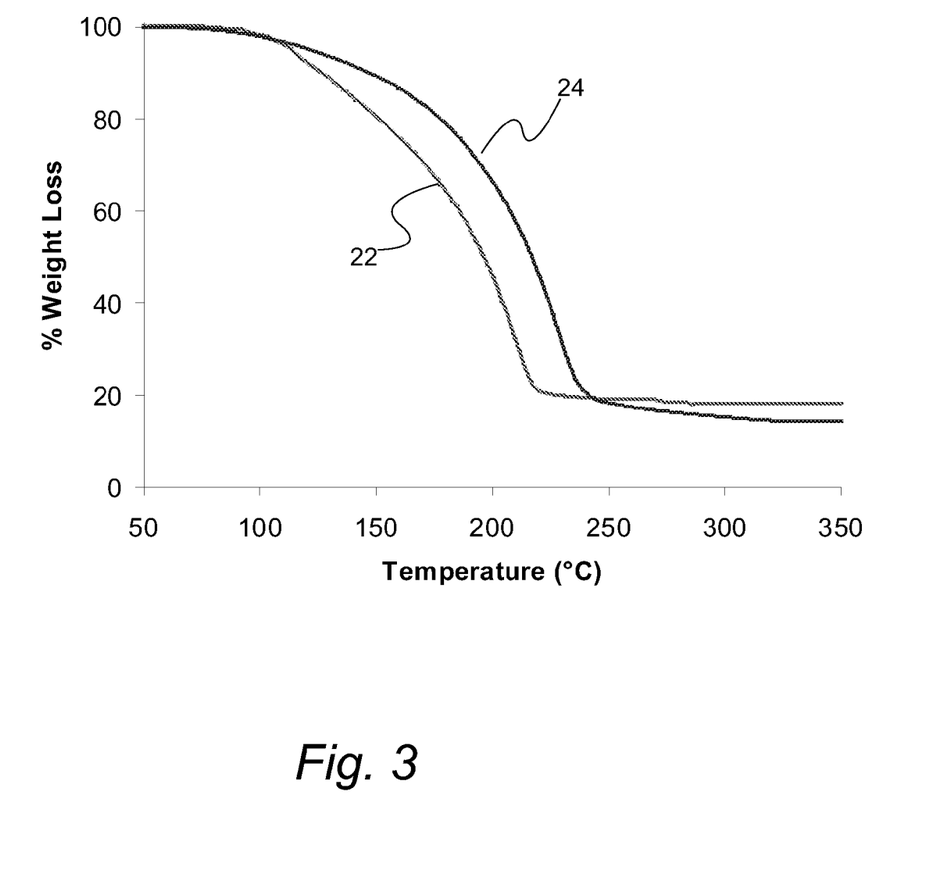
FIG. 3 provides TGA traces for compounds 22 and 24 from 50 to 350° C. at 10° C./min.

All four compounds are volatile. Complexes 22 and 23 sublime, and 24 and 25 distill, at ~90 and 105° C./0.05 Torr, respectively. Complexes 22 and 23 melt at or just above their sublimation temperatures (melting points; 22=90-92° C., 23=94-97° C.) and thus sublime from liquids. In preparative scale sublimation studies, samples of 22 and 23 left nonvolatile sublimation residues of less than 0.5% and maintained sublimation recoveries of more than 98%. Trace amounts of nonvolatile residues were observed for 24 and 25; however the recoveries were poor due to the handling difficulties associated with the sticky, viscous liquids. Accurate screening of the thermal stability of 22-25 by melting point tube experiments was impossible due to their dark color and paramagnetic $^1$H NMR spectra. Despite the air and moisture sensitivity, 22 and 24 were selected for further evaluations by TGA studies to establish their suitability as potential ALD precursors. The TGA traces are shown in FIG. 3. Both compounds show single step sublimations in the range of 90-242° C. with nonvolatile residues of 18.1 and 14.4%, respectively. The brief initial air exposure of the samples may lead to artificially high residue remaining at the end of the TGA.

2.4 Experimental Section
General Considerations.

All reactions were performed under argon using either glovebox or Schlenk line techniques. The secondary amide ligands $L^{tBu,tBu}H$, $L^{iPr,tBu}H$, $L^{Me,tBu}H$, $L^{tBu,iPr}H$, $L^{iPr,iPr}H$, and $L^{Me,iPr}H$ were prepared as described in section 1.

Preparation of $Cr(L^{tBu,tBu})_2(4\text{-}tBupy)_3$ (17).

A 100 mL Schlenk flask, equipped with a magnetic stir bar and a rubber septum, was charged with anhydrous chromium (II) chloride (0.250 g, 2.03 mmol) and tetrahydrofuran (50 mL). To the gray suspension was added 4-tert-butylpyridine (0.90 mL, 6.10 mmol) and the resultant green solution was stirred at ambient temperature for 2 h. In a separate Schlenk flask, $L^{tBu,tBu}K$ (4.06 mmol) was prepared by the slow addition of potassium hydride (0.179 g, 4.46 mmol) into a solution of $L^{tBu,tBu}H$ (0.639 g, 4.06 mmol) in tetrahydrofuran (20 mL). The resultant colorless solution was stirred at ambient temperature for 12 h and then added slowly by a cannula to the former in small portions. The resultant black solution was stirred at ambient temperature for 18 h. The volatile components were removed under reduced pressure to yield a greenish brown solid. This solid was extracted with hexane (60 mL) and was filtered through a 2-cm pad of Celite on a coarse glass frit. The hexane extract was concentrated to a volume of about 25 mL and was stored at −20° C. to afford 17 as dark green crystals (0.844 g, 54%): mp 189-192° C.

Preparation of $[Cr(L^{tBu,tBu})_2]_2$ (18).

As-prepared dark green crystalline solid 17 (0.500 g, 0.649 mmol) was sublimed at 122° C./0.05 Torr to afford 18 as orange crystals (0.162 g, 68%): mp 201-203° C.

Preparation of $[Cr(L^{iPr,tBu})_2]_2$ (19).

A 100 mL Schlenk flask, equipped with a magnetic stir bar and a rubber septum, was charged with $L^{iPr,tBu}H$ (0.467 g, 3.26 mmol) and tetrahydrofuran (20 mL). To this stirred solution at ambient temperature was slowly added potassium hydride (0.144 g, 3.59 mmol) and the resultant colorless solution was stirred for 3 h. This solution was then added slowly by a cannula to a stirred solution of anhydrous chromium(II) chloride (0.200 g, 1.63 mmol) and 4-tert-butylpyridine (0.72 mL, 4.88 mmol) in tetrahydrofuran (30 mL). The resultant yellow-brown solution was stirred at ambient temperature for 18 h and the volatile components were then removed under reduced pressure to obtain a yellow-brown semisolid. This solid was sublimed at 120° C./0.05 Torr to afford 19 as orange crystals (0.264 g, 48%): mp 344-347° C.

Preparation of $[Cr(L^{Me,tBu})_2]_2$ (20).

In a fashion similar to the preparation of 19, treatment of anhydrous chromium(II) chloride (0.200 g, 1.63 mmol) in tetrahydrofuran (30 mL) with 4-tert-butylpyridine (0.72 mL, 4.88 mmol) followed by $L^{Me,tBu}K$ (prepared from $L^{Me,tBu}H$ (0.375 g, 3.26 mmol) and potassium hydride (0.144 g, 3.59 mmol) in tetrahydrofuran (20 mL)) for 18 h at ambient temperature afforded a yellow-brown solution. The brown solid resulting upon removal of volatile components was sublimed at 105° C./0.05 Torr to afford 20 as orange crystals (0.372 g, 82%): mp 247-250° C.

Preparation of $[Cr(L^{tBu,iPr})_2]_2$ (21).

In a fashion similar to the preparation of 19, treatment of anhydrous chromium(II) chloride (0.200 g, 1.63 mmol) in tetrahydrofuran (30 mL) with 4-tert-butylpyridine (0.72 mL, 4.88 mmol) followed by $L^{tBu,iPr}K$ (prepared from $L^{tBu,iPr}H$ (0.467 g, 3.26 mmol) and potassium hydride (0.144 g, 3.59 mmol) in tetrahydrofuran (20 mL)) for 18 h at ambient temperature afforded a yellow-brown solution. The brown solid resulting upon removal of volatile components was sublimed at 125° C./0.05 Torr to afford 21 as yellow crystals (0.260 g, 48%): mp 347-350° C.

Preparation of $Cr(L^{iPr,tBu})_3$ (22).

A 100 mL Schlenk flask, equipped with a magnetic stir bar and a rubber septum, was charged with chromium(III) chloride (0.500 g, 3.16 mmol), $L^{iPr,tBu}H$ (1.357 g, 9.47 mmol), and tetrahydrofuran (50 mL). To this stirred mixture at ambient temperature was added a 1.6 M solution of methyllithium in diethyl ether (6.00 mL, 9.60 mmol). The deep green reaction mixture was stirred for 18 h at ambient temperature. The volatile components were then removed under reduced pressure and the resultant blue solid was dissolved in hexane (40 mL). The solution was filtered through a 1-cm pad of Celite on a coarse glass frit, and a dark green paste was obtained upon removal of hexane from the filtrate under reduced pressure. The crude product was sublimed at 92° C./0.05 Torr to afford 22 as dark green crystals (1.058 g, 70%): mp 90-92° C.

Preparation of $Cr(L^{Me,tBu})_3$ (23).

In a fashion similar to the preparation of 22, treatment of chromium(III) chloride (0.500 g, 3.16 mmol) and $L^{Me,tBu}H$ (1.091 g, 9.47 mmol) with a 1.6 M solution of methyllithium in diethyl ether (6.00 mL, 9.60 mmol) afforded 23 as dark green crystals upon sublimation at 90° C./0.05 Torr (0.822 g, 66%): mp 94-97° C.

Preparation of $Cr(L^{iPr,iPr})_3$ (24).

In a fashion similar to the preparation of 22, treatment of chromium(III) chloride (0.500 g, 3.16 mmol) and $L^{iPr,iPr}H$ (1.224 g, 9.47 mmol) with a 1.6 M solution of methyllithium in diethyl ether (6.00 mL, 9.60 mmol) afforded a dark green paste upon removal of volatile components under reduced pressure. This was then extracted with toluene (40 mL) and filtered through a 1-cm pad of Celite on a coarse glass frit. A dark green viscous liquid was obtained upon removal of toluene under reduced pressure and was then distilled using a Kugelrohr short-path vacuum distillation apparatus at 105° C./0.05 Torr to afford 24 as a dark green liquid (0.744 g, 54%).

Preparation of $Cr(L^{Me,iPr})_3$ (25).

In a fashion similar to the preparation of 22, treatment of chromium(III) chloride (0.500 g, 3.16 mmol) and $L^{Me,iPr}H$ (0.958 g, 9.47 mmol) with a 1.6 M solution of methyllithium in diethyl ether (6.00 mL, 9.60 mmol) afforded 25 as a dark green viscous liquid upon distillation at 105° C./0.05 Torr (0.478 g, 43%).

3. Preparation of Zirconium and Hafnium Complexes Containing Amidate Ligands

3.1 Synthesis of Zirconium and Hafnium Complexes.

Treatment of tetrakis(dimethylamido)zirconium with four equivalents of $L^{Me,tBu}H$, $L^{iPr,iPr}H$, or $L^{Me,iPr}H$ in refluxing toluene, followed by vacuum sublimation of the crude products, afforded $Zr(\eta^2\text{-}L^{Me,tBu})_4$ (26, 81%), $Zr(\eta^2\text{-}L^{iPr,iPr})_4$ (27, 87%), and $Zr(\eta^2\text{-}L^{Me,iPr})_4$ (28, 51%), respectively, as colorless crystalline solids (eq 7). Similar treatment of tetrakis(dimethylamido)hafnium with $L^{Me,tBu}H$, $L^{iPr,iPr}H$, or $L^{Me,iPr}H$ afforded $Hf(\eta^2\text{-}L^{Me,tBu})_4$ (29, 83%), $Hf(\eta^2\text{-}L^{iPr,iPr})_4$ (30, 79%) and $Hf(\eta^2\text{-}L^{Me,iPr})_4$ (31, 67%), as colorless crystalline solids (eq 7). All compounds 26-31 are volatile and were isolated as white crystalline solids by sublimation at 120, 115, 110, 125, 115, and 105° C./0.05 Torr, respectively.

(7)

-continued

26, M = Zr, R = Me, R' = tBu, 81%
27, M = Zr, R = iPr, R' = iPr, 87%
28, M = Zr, R = Me, R' = iPr, 51%
29, M = Hf, R = Me, R' = tBu, 83%
30, M = Hf, R = iPr, R' = iPr, 79%
31, M = Hf, R = Me, R' = iPr, 67%

The structural assignments for 26-31 were based upon spectral and analytical data as well as X-ray crystal structure determinations for 26, 28, and 31. Due to poor quality crystals, structure determinations for 27 and 30 were not possible and only a low precision X-ray crystal structure was obtained for 29, which provided an unambiguous identification for a structure similar to that of 26. Complexes 26, 28, 29, and 31 are monomeric in the solid state with eight-coordinate metal centers surrounded by four $\eta^2$-amidate ligands, while complexes 27 and 30 should possess similar structures based on spectral and analytical data. The $^1$H and $^{13}$C{$^1$H} NMR spectra of 26-31 in benzene-$d_6$ are consistent with the solid state structure assignments and show only one set of resonances for all four amidate ligands in the same chemical environment.

3.2 Volatility and Thermal Stability Study.

Assessment of the volatility and thermal stability of compounds 26-31 was focused toward establishing them as a new class of ALD and CVD precursors. All compounds were subjected to a careful examination of melting point, decomposition temperature, as well as volatility behavior in preparative sublimation experiments. Attempts to obtain accurate TGA data were unsuccessful due to the high air and moisture sensitivity of the compounds. The preparative sublimation and decomposition temperature data for 26-31 are summarized in Table 3.

TABLE 3

Preparative Sublimation Data and Decomposition Temperatures for 26-31.

| Compound | Preparative Sublimation Temperature (° C./0.05 Torr) | % Recovery | % Residue | Decomposition Temperature (° C.) |
|---|---|---|---|---|
| 26 | 135 | 92.2 | 3.1 | 280 |
| 27 | 130 | 84.5 | 1.4 | 335 |
| 28 | 130 | 96.4 | 0.9 | 270 |
| 29 | 140 | 94.9 | 1.1 | 300 |
| 30 | 135 | 86.8 | 1.3 | 360 |
| 31 | 130 | 95.8 | 0.7 | 290 |

In the thermal stability study, a few milligrams of each sample was sealed under the exclusion of oxygen or moisture in argon-filled capillary tubes and heated at the rate of 5° C./min from 25° C. until it showed discoloration as the initial qualitative evidence of decomposition. All compounds undergo abrupt visual discoloration upon decomposition from their liquid state. All compounds turn into orange-brown liquids upon decomposition. The reported thermal decomposition temperatures of the compounds (Table 3) were established unambiguously by evaluating their thermal stability at a temperature 5° C. below their decomposition points. This experiment was performed by heating two sets of samples in sealed melting point tubes to 5° C. below their visual decomposition points and by subsequently remelting the first set of samples and by taking $^1$H NMR spectra of the other set of samples. The $^1$H NMR spectra of the preheated samples showed minor or no evidence of decomposition. Compounds 26-31 melt at 255-258, 285-288, 206-209, 255-258, 283-286, and 207-210° C., respectively, and decompose at 280, 335, 270, 300, 360, and 290° C., respectively.

In preparative sublimation studies of 26-31, 0.5-1.0 g of a previously sublimed sample was sublimed at 135, 130, 130, 140, 135, and 130° C./0.05 Torr, respectively, and the percent recoveries were in the range of 84.5-96.4% (Table 3). Complete sublimation of the samples was achieved within 4-6 hours by conducting the experiments at temperatures about 20° C. higher than their sublimation temperatures reported in the experimental section. Nonvolatile residues as a percentage of initial sample weight were 3.1, 1.4, 0.9, 1.1, 1.3, and 0.7%, respectively, which indicates an insignificant amount of decomposition during sublimation. In general, all compounds follow similar sublimation behavior and demonstrate high volatility at low temperatures with excellent levels of recovery and residue, which indicates that they may serve as good CVD and ALD precursors.

3.3 Experimental Section

General Considerations.

All reactions were performed under argon using standard glovebox and Schlenk line techniques. Preparation of the secondary amide proligands $L^{Me,tBu}H$, $L^{iPr,iPr}H$, and $L^{Me,tBu}H$ was described in section 1.

Preparation of Zr($L^{Me,tBu}$)$_4$ (26).

A 100 mL Schlenk flask, fitted with a reflux condenser, was charged with tetrakis(dimethylamido)zirconium (0.200 g, 0.748 mmol) and $L^{Me,tBu}H$ (0.344 g, 2.99 mmol). With vigorous stirring, 20 mL of toluene was added and the colorless reaction mixture was then refluxed for 3 h. Upon cooling to room temperature, the volatile components were removed under reduced pressure to give a white solid. Sublimation of the crude solid at 120° C./0.05 Torr afforded 26 as colorless crystals (0.332 g, 81%): mp 255-258° C.

Preparation of Zr($L^{iPr,iPr}$)$_4$ (27).

In a fashion similar to the preparation of 26, treatment of tetrakis(dimethylamido)zirconium (0.200 g, 0.748 mmol) with $L^{iPr,iPr}H$ (0.386 g, 2.99 mmol) in refluxing toluene (20 mL) for 3 h afforded 27 as a colorless crystalline solid (0.393 g, 87%) upon sublimation at 115° C./0.05 Torr: mp 285-288° C.

Preparation of Zr($L^{Me,iPr}$)$_4$ (28).

A 100 mL Schlenk flask, fitted with a reflux condenser, was charged with tetrakis(dimethylamido)zirconium (0.200 g, 0.748 mmol) and toluene (10 mL). A solution of $L^{Me,iPr}H$ (0.302 g, 2.99 mmol) in toluene (10 mL) was added slowly and the resultant mixture was refluxed for 3 h. Upon cooling to room temperature, the volatile components were removed under reduced pressure and sublimation of the crude solid at 110° C./0.05 Torr afforded 28 as colorless crystals (0.188 g, 51%): mp 206-209° C.

Preparation of Hf($L^{Me,tBu}$)$_4$ (29).

In a fashion similar to the preparation of 26, treatment of tetrakis(dimethylamido)hafnium (0.200 g, 0.563 mmol) with $L^{Me,tBu}H$ (0.260 g, 2.25 mmol) in refluxing toluene (15 mL) for 3 h afforded 29 as a colorless crystalline solid (0.297 g, 83%) upon sublimation at 125° C./0.05 Torr: mp 255-258° C.

Preparation of Hf($L^{iPr,iPr}$)$_4$ (30).

In a fashion similar to the preparation of 26, treatment of tetrakis(dimethylamido)hafnium (0.200 g, 0.563 mmol) with $L^{iPr,iPr}H$ (0.291 g, 2.25 mmol) in refluxing toluene (15 mL) for 3 h afforded 30 as a colorless crystalline solid (0.308 g, 79%) upon sublimation at 115° C./0.05 Torr: mp 283-286° C.

Preparation of $Hf(L^{Me,iPr})_4$ (31).

In a fashion similar to the preparation of 28, treatment of tetrakis(dimethylamido)hafnium (0.200 g, 0.563 mmol) with $L^{Me,iPr}H$ (0.228 g, 2.25 mmol) in refluxing toluene (15 mL) for 3 h afforded 31 as colorless crystals (0.219 g, 67%) upon sublimation at 105° C./0.05 Torr: mp 207-210° C.

4. Preparation of Carbohydrazide Complexes of Mid to Late First Row Transition Metals.

4.1 Synthesis of Ligands.

The carbohydrazide ligands N',N'-dimethylpivalohydrazide ($L^{tBu,NMe2}H$), N',N'-dimethylisobutyrohydrazide ($L^{iPr,NMe2}H$), and N',N'-dimethylacetohydrazide ($L^{Me,NMe2}H$) were prepared in a manner similar to the amidate ligands set forth above by using commercially available carboxylic acid chlorides and 1,1-dimethylhydrazine in the presence of triethylamine as a base (eq 8). $L^{tBu,NMe2}H$ and $L^{iPr,NMe2}H$ were isolated from sublimation at 65 and 60° C./0.05 Torr, respectively, while the liquid $L^{Me,NMe2}H$ was vacuum distilled at 70° C./0.05 Torr.

(8)

4.2 Synthesis of Carbohydrazide Complexes.

Treatment of anhydrous copper(II) chloride with two equivalents of $L^{tBu,NMe2}K$, $L^{iPr,NMe2}K$ or $L^{Me,NMe2}K$, prepared in situ from the corresponding carbohydrazide ligands and potassium hydride, in tetrahydrofuran afforded the mononuclear copper(II) bis-carbohydrazide complexes $Cu(L^{tBu,NMe2})_2$ (32, 75%), $Cu(L^{iPr,NMe2})_2$ (33, 51%), and $Cu(L^{Me,NMe2})_2$ (34, 23%), respectively, as maroon crystals (eq 9). Compound 32 was isolated in high yield from sublimation at 70° C./0.05 Torr, whereas sublimation yields for 33 (75° C./0.05 Torr) and 34 (80° C./0.05 Torr) were substantially lower. Similar treatment of cobalt(II) chloride with $L^{tBu,NMe2}K$ afforded $Co(L^{tBu,NMe2})_2$ (35, 57%) as red crystals upon sublimation at 75° C./0.05 (eq 9). Treatment of the mono acetonitrile adduct of nickel(II) chloride with two equivalents of $L^{tBu,NMe2}K$ or $L^{iPr,NMe2}K$ afforded the mononuclear bis-carbohydrazide complexes $Ni(L^{tBu,NMe2})_2$ (36, 76%) and $Ni(L^{iPr,NMe2})_2$ (37, 62%), respectively, as orange color crystals upon sublimation at 70° C. and 80° C./0.05 Torr, respectively (eq 10).

(9)

32, M = Cu, R = tBu, 75%
33, M = Cu, R = iPr, 51%
34, M = Cu, R = Me, 23%
35, M = Co, R = tBu, 57%

(10)

36, R = tBu, 76%
37, R = iPr, 62%

Treatment of the tetrahydrofuran adduct of chromium(II) chloride with two equivalents of $L^{tBu,NMe2}K$ afforded the mononuclear bis-pivalohydrazide complex $Cr(L^{tBu,NMe2})_2$ (38, 62%) as orange crystals from hexane solution (eq 11). Treatment of anhydrous iron(II) chloride or manganese(II) bromide with two equivalents of $L^{tBu,NMe2}K$ in tetrahydrofuran afforded the corresponding dinuclear tetrakis-pivalohydrazide complexes $[Fe(L^{tBu,NMe2})_2]_2$ (39, 28%) and $[Mn(L^{tBu,NMe2})_2]_2$ (40, 12%), respectively (eq 12). Similar treatment of cobalt(II), chromium(II), iron(II), or manganese(II) with the less sterically encumbered $L^{iPr,NMe2}K$ or $L^{Me,NMe2}K$ ligands did not generate isolable products (in more than 5% yields), which can be attributed to dimer or oligomer formation. All reaction manipulations and the crystalline products were handled under argon atmospheres except crystals of 32 and 36, which are stable in air, while 33, 34, and 37 react slowly with moisture in the air.

(11)

38, 62%

(12)

39, M = Fe, X = Cl, 28%
40, M = Mn, X = Br, 12%

The structural assignments for 32-40 are based upon spectral and analytical data. In addition, X-ray crystal structure determinations were carried out for all compounds, although only a low precision X-ray crystal structure determination was obtained for 40, which demonstrated a dinuclear structure similar to that of the iron compound 39. The $^1$H NMR spectra of 32-35 and 38 show broad and magnetically shifted resonances due to their paramagnetic nature, while the spectra of 36 and 37 in benzene-$d_6$ consist of sharp signals for the ligand substituents, which can be attributed to spin-paired, diamagnetic $d^8$ nickel(II) centers.

4.3 Experimental Section

General Considerations.

All metal-organic reactions were performed under argon using standard glovebox and Schlenk line techniques. NiCl$_2$.CH$_3$CN was prepared according to a published procedure. (Reedijk, J.; Groeneveld, W. L. *Recl. Tray. Chim. Pays-Bas* 1968, 87, 552).

Preparation of N',N'-dimethylpivalohydrazide ($L^{tBu,NMe2}$H).

A 500-mL round bottomed flask was charged with 1,1-dimethylhydrazine (3.88 mL, 50 mmol), triethylamine (7.52 mL, 53 mmol), and diethyl ether (250 mL). To this stirred solution at 0° C. was slowly added pivaloylchloride (6.28 mL, 50 mmol). The resultant white suspension was stirred at ambient temperature for 18 h. This suspension was then filtered through a sintered glass funnel to afford a colorless solution. The volatile components were then removed and the resultant white solid was sublimed at 65° C./0.05 Torr to afford $L^{tBu,NMe2}$H as colorless crystals (6.95 g, 96%): mp 120-122° C.

Preparation of N',N'-dimethylisobutyrohydrazide ($L^{iPr,NMe2}$H).

In a fashion similar to the preparation of $L^{tBu,NMe2}$H, treatment of a diethyl ether (250 mL) solution of 1,1-dimethylhydrazine (3.88 mL, 50 mmol) and triethylamine (7.52 mL, 53 mmol) with isobutyryl chloride (5.39 mL, 50 mmol) afforded $L^{iPr,NMe2}$H as colorless crystals upon crystallization from Et$_2$O and subsequent sublimation at 60° C./0.05 Torr (6.12 g, 94%): mp 94-96° C.

Preparation of N',N'-dimethylacetohydrazide ($L^{Me,NMe2}$H).

A 500-mL round bottom flask was charged with 1,1-dimethylhydrazine (3.88 mL, 50 mmol), triethylamine (7.52 mL, 53 mmol), and diethyl ether (250 mL). To this stirred solution at 0° C. was slowly added acetyl chloride (3.63 mL, 50 mmol). The resultant white suspension was stirred at ambient temperature for 18 h. This suspension was then filtered through a sintered glass funnel to afford a colorless solution. The volatile components were then removed and the resultant pale yellow oil was distilled at 70° C./0.05 Torr (lit. bp$^{148c}$ 98° C./16 Torr) to afford $L^{Me}$H as a colorless liquid (4.34 g, 85%).

Preparation of Cu($L^{tBu,NMe2}$)$_2$ (32).

A 100 mL Schlenk flask, equipped with a magnetic stir bar and a rubber septum, was charged with $L^{tBu,NMe2}$H (2.102 g, 14.58 mmol) and tetrahydrofuran (50 mL). To this stirred solution at ambient temperature was slowly added potassium hydride (0.614 g, 15.31 mmol) and the resultant colorless solution was stirred for 12 h. This solution was then slowly added over 30 min to a stirred suspension of anhydrous copper(II) chloride (1.000 g, 7.29 mmol) in tetrahydrofuran (40 mL). The resultant purple solution was stirred an additional 30 min at ambient temperature. The volatile components were then removed under reduced pressure and the resultant maroon solid was dissolved in toluene (50 mL). The solution was filtered through a 1-cm pad of Celite on a coarse glass frit, and toluene was then removed under reduced pressure. An analytically pure sample of 32 was obtained as maroon crystals by sublimation at 70° C./0.05 Torr (1.913 g, 75%): mp 137-139° C.

Preparation of Cu($L^{iPr,NMe2}$)$_2$ (33).

In a fashion similar to the preparation of 32, treatment of anhydrous copper(II) chloride (1.000 g, 7.29 mmol) in tetrahydrofuran (40 mL) with $L^{iPr,NMe2}$K (prepared from $L^{iPr,NMe2}$H (1.898 g, 14.58 mmol) and potassium hydride (0.614 g, 15.31 mmol) in tetrahydrofuran (50 mL)) for a total of 1 h at ambient temperature afforded 33 (1.197 g, 51%) as maroon crystals after sublimation at 75° C./0.05 Torr: mp 118-121° C.

Preparation of Cu($L^{Me,NMe2}$)$_2$ (34).

In a fashion similar to the preparation of 32, treatment of anhydrous copper(II) chloride (1.000 g, 7.29 mmol) in tetrahydrofuran (40 mL) with $L^{Me,NMe2}$K (prepared from $L^{Me,NMe2}$H (1.489 g, 14.58 mmol) and potassium hydride (0.614 g, 15.31 mmol) in tetrahydrofuran (70 mL)) for a total of 1 h at ambient temperature afforded 34 (0.446 g, 23%) as maroon crystals after sublimation at 80° C./0.05 Torr: mp 184-187° C.

Preparation of Co($L^{tBu,NMe2}$)$_2$ (35).

A 100 mL Schlenk flask, equipped with a magnetic stir bar and a rubber septum, was charged with $L^{tBu,NMe2}$H (2.221 g, 15.40 mmol) and tetrahydrofuran (50 mL). To this stirred solution at ambient temperature was slowly added potassium hydride (0.649 g, 16.17 mmol) and the resultant colorless solution was stirred for 12 h. This solution was then slowly added over 30 min to a stirred suspension of anhydrous cobalt (II) chloride (1.000 g, 7.70 mmol) in tetrahydrofuran (40 mL). The resultant black solution was stirred for 5 h at ambient temperature. The volatile components were then removed under reduced pressure and the resultant black paste was dissolved in toluene (50 mL). The solution was filtered through a 1-cm pad of Celite on a coarse glass frit, and toluene was then removed under reduced pressure. An analytically pure sample of 35 was obtained by sublimation at 75° C./0.05 Torr to afford red crystals (1.516 g, 57%): mp 137-140° C.

Preparation of Ni($L^{tBu,NMe2}$)$_2$ (36).

A 100 mL Schlenk flask, equipped with a magnetic stir bar and a rubber septum, was charged with $L^{tBu,NMe2}$H (1.690 g, 11.72 mmol) and tetrahydrofuran (50 mL). To this stirred solution at ambient temperature was slowly added potassium hydride (0.494 g, 12.31 mmol) and the resultant colorless solution was stirred for 12 h. This solution was then slowly added to a stirred suspension of NiCl$_2$.CH$_3$CN (1.000 g, 5.86 mmol) in tetrahydrofuran (30 mL). The resultant yellow solution was stirred for 18 h at ambient temperature. The volatile components were then removed under reduced pressure and the resultant yellow solid was dissolved in toluene (50 mL). The solution was filtered through a 1-cm pad of Celite on a coarse glass frit, and toluene was then removed under reduced pressure. An analytically pure sample of 36 was obtained by sublimation at 70° C./0.05 Torr to afford orange colored crystals (1.537 g, 76%): mp 140-142° C.

Preparation of Ni(L$^{iPr,NMe2}$)$_2$ (37).

In a fashion similar to the preparation of 36, treatment of NiCl$_2$.CH$_3$CN (1.000 g, 5.86 mmol) in tetrahydrofuran (30 mL) with L$^{iPr,NMe2}$K (prepared from L$^{iPr,NMe2}$H (1.526 g, 11.72 mmol) and potassium hydride (0.494 g, 12.31 mmol) in tetrahydrofuran (50 mL)) for a 18 h at ambient temperature afforded 37 (1.152 g, 62%) as orange colored crystals upon sublimation at 80° C./0.05 Torr: mp 125-128° C.

Preparation of Cr(L$^{tBu,NMe2}$)$_2$ (38).

A 200 mL Schlenk flask, equipped with a magnetic stir bar and a reflux condenser, was charged with anhydrous chromium(II) chloride (1.000 g, 8.14 mmol) and tetrahydrofuran (40 mL). This suspension was refluxed for 1 h. Upon cooling, a solution of L$^{tBu,NMe2}$K (prepared gtp, L$^{tBu,NMe2}$H (2.347 g, 16.27 mmol) and potassium hydride (0.685 g, 17.09 mmol) in tetrahydrofuran (50 mL)) was cannulated slowly into the green suspension over a period of 30 min and the resultant brown solution was stirred for 12 h at ambient temperature. The volatile components were then removed under reduced pressure and the resultant brown solid was dissolved in hexane (60 mL). The solution was filtered through a 1-cm pad of Celite on a coarse glass frit, and orange crystals of 38 formed from the warm concentrated solution upon cooling to room temperature. More crystals of the product were obtained from the concentrated mother liquor at −25° C. (1.708 g, 62%): mp 143-146° C.

Preparation of [Fe(L$^{tBu,NMe2}$)$_2$]$_2$ (39).

A 100 mL Schlenk flask, equipped with a magnetic stir bar and a rubber septum, was charged with L$^{tBu,NMe2}$H (1.051 g, 7.29 mmol) and tetrahydrofuran (25 mL). To this stirred solution at ambient temperature was slowly added potassium hydride (0.307 g, 7.66 mmol) and the resultant colorless solution was stirred for 12 h. This solution was then slowly added over 30 min to a stirred suspension of anhydrous iron (II) chloride (0.464 g, 3.64 mmol) in tetrahydrofuran (20 mL). The resultant pale blue solution was stirred for 3 h and the volatile components were then removed under reduced pressure. The resultant pale blue paste was dissolved in toluene (50 mL) and the pale green solution was filtered through a 1-cm pad of Celite on a coarse glass frit. Toluene was then removed under reduced pressure to afford 39 as a gray solid (1.084 g, 87%). Pale green crystals of 39 suitable for single crystal X-ray crystallographic analysis were obtained by sublimation at 85° C./0.05 Torr (0.349 g, 28%).

Preparation of [Mn(L$^{tBu,NMe2}$)$_2$]$_2$ (40).

A 100 mL Schlenk flask, equipped with a magnetic stir bar and a rubber septum, was charged with anhydrous manganese (II) bromide (0.791 g, 3.64 mmol) and tetrahydrofuran (20 mL). To this stirred suspension at ambient temperature was slowly added L$^{tBu,NMe2}$K (prepared from L$^{tBu,NMe2}$H (1.051 g, 7.29 mmol) and potassium hydride (0.307 g, 7.66 mmol) in tetrahydrofuran (25 mL)). The resultant white suspension was stirred for 18 h and the volatile components were then removed under reduced pressure. The resultant white solid was dissolved in toluene (50 mL) and filtered through a 1-cm pad of Celite on a coarse glass frit. Toluene was then removed under reduced pressure to afford 40 as a pale brown solid (1.093 g, 88%). Colorless crystals of 40 suitable for X-ray crystallographic analysis were obtained from a concentrated solution in toluene at −25° C. (0.149 g, 12%).

5. Thin Film Deposition

Copper Film Deposition.

An R-75 ALD reactor manufactured by Picosun Oy was used for thin film deposition experiments. The reactor was operated under a flow of nitrogen at a pressure of 1-2 mbar. The deposition of copper metal films by ALD was studied by employing bis(N',N'-dimethylpivalohydrazato)copper(II), (CuL2), as the copper source and formic acid as the reducing agent. In initial growth trials, the sublimation temperature of CuL2 was found to be optimum at 105° C. at the reactor pressure. The substrate temperatures were held between 150 and 350° C. Nitrogen was used as both the carrier and purge gas and was obtained for air using a Taxol GeniSys nitroGenerator. Deposition experiments were performed using a range of CuL2 pulse lengths (0.5-5.0 seconds), formic acid pulse (0.1-3.0 seconds), and nitrogen purge lengths (3.0-5.0 seconds) to determine the extent of surface saturation. Films were deposited on Si(100) with and without HF treatment, Corning Eagle XG glass, and TaN substrates obtained from Silicon Quest International. One substrate, one quarter of a 3-inch wafer, was used in each deposition experiment.

Nickel Film Deposition.

An R-75 ALD reactor manufactured by Picosun Oy was used for thin film deposition experiments. The reactor was operated under a flow of nitrogen at a pressure of 1-2 mbar. The deposition of copper metal films by ALD was studied by employing bis(N',N'-dimethylpivalohydrazato)nickel(II), (NiL2), as the copper source and formic acid as the reducing agent. In initial growth trials, the sublimation temperature of NiL2 was found to be optimum at 105° C. at the reactor pressure. The substrate temperatures were held between 225 and 400° C. Nitrogen was used as both the carrier and purge gas and was obtained for air using a Taxol GeniSys nitroGenerator. Deposition experiments were performed using a range of NiL2 pulse lengths (0.5-5.0 seconds), formic acid pulse (0.1-3.0 seconds), and nitrogen purge lengths (3.0-5.0 seconds) to determine the extent of surface saturation. Films were deposited on Si(100) with and without HF treatment, Corning Eagle XG glass, and TaN substrates obtained from Silicon Quest International. One substrate, one quarter of a 3-inch wafer, was used in each deposition experiment.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound having formula 1:

$$M_x L_y \qquad 1$$

wherein

M is a transition metal;

x is 1 or 2;

y is an integer from 1 to 4;

L is N(R$_1$R$_2$)—N=C(R$_3$)—O or OC(R$_4$)—N(R$_5$);

R$_1$, R$_2$, R$_3$, R$_4$, R$_5$ are each independently hydrogen, C$_{1-12}$ alkyl or C$_{6-12}$ aryl, Si(R$_6$)$_3$, or Ge(R$_6$)$_3$; and R$_6$ is hydrogen, C$_{1-12}$ alkyl or C$_{6-12}$ aryl, wherein y is 2 when x is 1 and y is 4 when x is 2.

2. The compound of claim 1 wherein M is a metal in a 1+, 2+, 3+, or 4+ oxidation state.

3. The compound of claim 1 having formula 2:

or geometric isomers thereof.

4. The compound of claim 3 wherein $R_1$, $R_2$, and $R_3$ are each independently hydrogen, methyl, ethyl, n-propyl, isopropyl, n-butyl, t-butyl, or sec-butyl.

5. The compound of claim 3 wherein M is Cu, Ni, Co, Cr, Mn, or Fe.

6. The compound of claim 3 having formula 3:

or geometric isomers thereof.

7. The compound of claim 6 wherein M is Cu, Ni, Co, Cr, Mn, or Fe.

8. The compound of claim 1 having formula 4:

or geometric isomers thereof
wherein $R_1$, $R_2$, $R_3$ are each independently hydrogen, methyl, ethyl, n-propyl, isopropyl, n-butyl, t-butyl, or sec-butyl; and
M is Mn or Fe.

9. The of claim 1 wherein L is: $OC(R_4)-N(R_5)$.

10. The compound of claim 1 having formula 5:

or geometric isomers thereof,
wherein $R_4$, $R_5$ are each independently hydrogen, methyl, ethyl, n-propyl, isopropyl, n-butyl, t-butyl, iso-butyl or sec-butyl.

11. The compound of claim 1 having formula 6:

or geometric isomers thereof,
wherein $R_4$, $R_5$ are each independently hydrogen, methyl, ethyl, n-propyl, isopropyl, n-butyl, t-butyl, iso-butyl or sec-butyl; and
----- is absent, a single bond between two M, or a multiple bond between two M.

12. The compound of claim 1 having formula 7:

or geometric isomers thereof;
wherein $R_4$, $R_5$ are each independently hydrogen, methyl, ethyl, n-propyl, isopropyl, n-butyl, t-butyl, iso-butyl or sec-butyl; and
----- is absent, a single bond between two M, or a multiple bond between two M.

* * * * *